United States Patent [19]
Endo et al.

[11] Patent Number: 6,063,898
[45] Date of Patent: May 16, 2000

[54] COMPOUNDS, POLYMERS OF THEM, PROCESSES FOR THE PREPARATION OF BOTH, AND COMPOSITIONS CONTAINING THE COMPOUNDS

[75] Inventors: Takeshi Endo, Yokohama; Hiroto Miyake, Ohtake, both of Japan

[73] Assignee: Daicel Chemical Industries, Ltd., Sakai, Japan

[21] Appl. No.: 09/125,161

[22] PCT Filed: Dec. 17, 1997

[86] PCT No.: PCT/JP97/04660

§ 371 Date: Aug. 13, 1998

§ 102(e) Date: Aug. 13, 1998

[87] PCT Pub. No.: WO98/27079

PCT Pub. Date: Jun. 25, 1998

[30] Foreign Application Priority Data

| Dec. 18, 1996 | [JP] | Japan | 8-353734 |
| Sep. 29, 1997 | [JP] | Japan | 9-281388 |
| Sep. 29, 1997 | [JP] | Japan | 9-281389 |
| Sep. 29, 1997 | [JP] | Japan | 9-281390 |
| Sep. 29, 1997 | [JP] | Japan | 9-281391 |

[51] Int. Cl.$^7$ ............................... C08G 59/68
[52] U.S. Cl. .................... 528/411; 528/367; 528/368; 528/420; 528/421
[58] Field of Search ................... 528/367, 368, 528/411, 420, 421

[56] References Cited

U.S. PATENT DOCUMENTS

| 3,245,950 | 4/1966 | Holm | 528/367 |
| 4,880,906 | 11/1989 | Esselborn et al. | 528/421 |

*Primary Examiner*—Melvyn I. Marquis
*Attorney, Agent, or Firm*—Morgan & Finnegan, L.L.P.

[57] ABSTRACT

The first aspect of the invention provides a novel compound containing a reactive functional group represented by formula (1)

$$R^2\text{—O—CO—NH—CH=CH—}R^1 \quad (1)$$

wherein $R^1$ represents a hydrogen atom, an aromatic hydrocarbon group, or a saturated or unsaturated aliphatic hydrocarbon group, $R^2$ represents a formula comprising alicyclic functionality.

The second aspect provides an active energy ray-curable unsaturated resin composition prepared by mixing a reaction product of the above-mentioned compound (1) with an unsaturated resin containing an acid group and with a diluent. The composition can be cured by active energy rays, and it can be used as an alkali developable and active energy ray-curable type resist resin composition.

The third aspect provides an active energy ray-polymerizable unsaturated resin composition obtainable by allowing to react an unsaturated compound (E) containing an alicyclic epoxy group represented by formula (1) with a colloidal silica (F) in the presence of a metal chelate and/or metal alkoxide (G). A powder-state active energy ray-polymerizable unsaturated resin composition is obtained by removing a solvent from the composition.

A fourth aspect of the invention provides a composition which comprises a copolymer of a specified polysiloxane-based macromonomer with a compound represented by formula (1), and an organic aluminum chelate compound, and the composition is curable at low-temperatures.

14 Claims, 2 Drawing Sheets

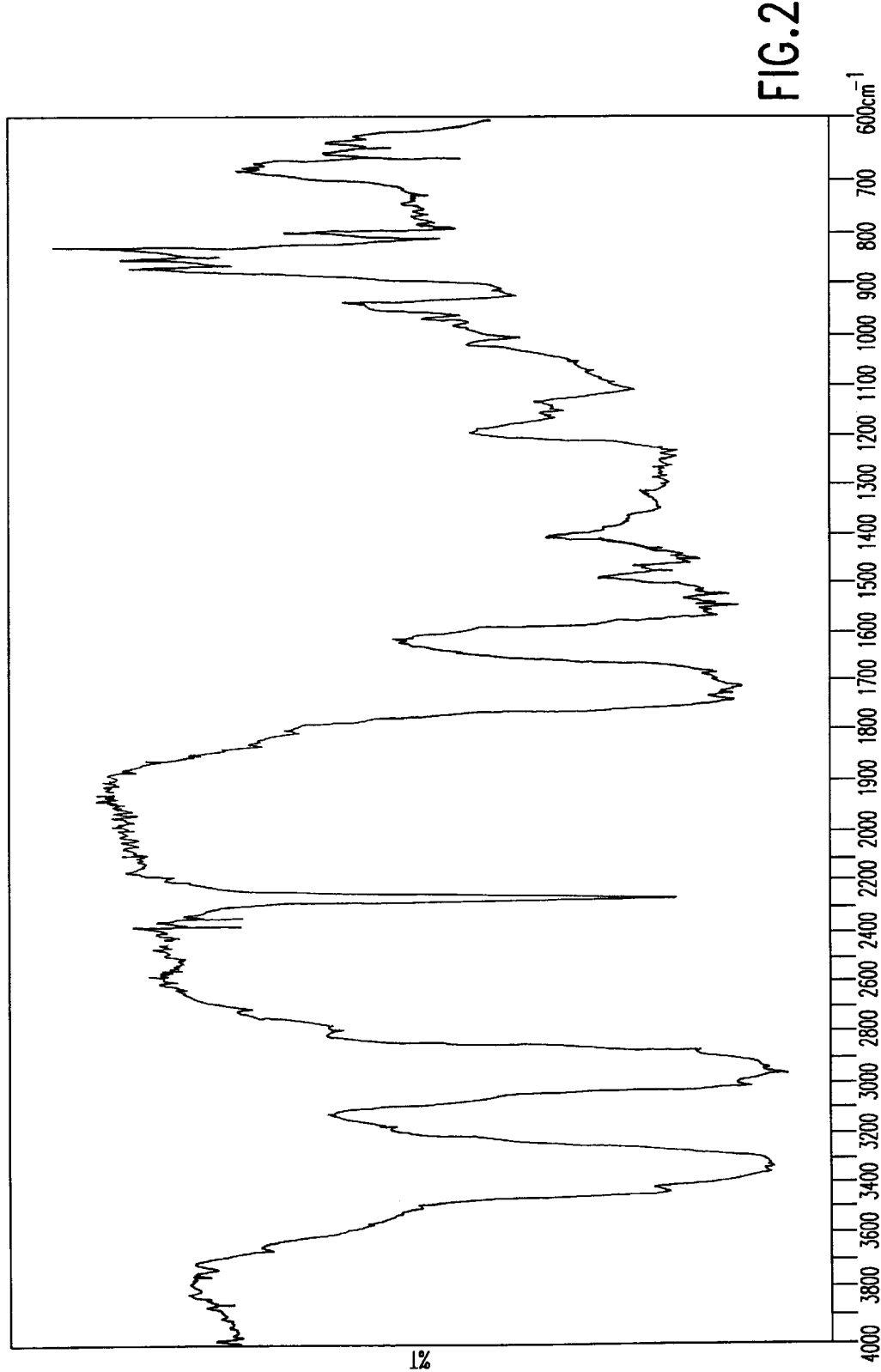

COMPOUNDS, POLYMERS OF THEM, PROCESSES FOR THE PREPARATION OF BOTH, AND COMPOSITIONS CONTAINING THE COMPOUNDS

TECHNICAL ART OF FIRST ASPECT OF THE INVENTION

First aspect of the invention relates to a novel compound containing a reactive functional group and the use thereof. In more detail, it relates to a novel compound which readily polymerizes solely or copolymerizes by heating or light irradiation, and which can be employed as a printing use, a resist for electronics, a coating, and an adhesive, etc.

BACKGROUND ART OF FIRST ASPECT OF THE INVENTION

There has been desired an improvement of dissolution degree in a photosensitive film, etc. with a progress of uses for a variety of printing plates and electronics. As a result pulled by such the market needs, a polymer industry remarkably progresses, and there are developed and employed a great variety of compounds and polymeric materials over a wide scope. In recent years, there has been particularly desired a development of more excellent compounds and polymeric materials with the progress of a shift to high function and performance in industrial products.

For example, in a field of resists for a printed circuit board, as a method for forming a resist in the printed circuit board, there has been developed a photographic method in which a desired resist pattern is formed by exposing a photosensitive film using a fixed pattern to light and by developing it.

Further, there has been employed a liquid-state resist from a viewpoint of price or characteristics not existing in the photosensitive film.

Still further, as a developing agent in the case of forming a resist, there have been conventionally employed a solvent-developing type and a diluted aqueous alkali solution-developing type in which there is employed a sodium carbonate aqueous solution, and a development is shifting to the use of the diluted aqueous alkali solution-developing type in view of a break of ozone gas layer and the influence on working surroundings.

Under such the market needs, there have been developed a compound having at least two reactive groups in the molecule, and a reactive oligomer or polymer having a plurality of reactive groups which are side chains for a thermosetting or photo-curable resin. In addition, there are investigated and developed a wide range of industrial uses in a variety of fields, and there is expected a development of new materials as functional resins other than those. Particularly, there are desired eagerly a development of a multi-functional monomer capable of polymerizing solely or copolymerizing with other compound containing unsaturated groups by heating or by irradiating the light such as an ultraviolet ray or an ionic radioactive ray, and a development of a monomer or a polymer which composes a curable resin which is employed for printing uses and as a resist for electronics, a coating, and an adhesive, etc. Particularly, there is desired eagerly a development of a monomer or a polymer therefrom which composes a resist which has a short developing time, and which is excellent in sensitivity, adhesion, heat resistance in a solder and, moreover hydrolysis resistance.

DISCLOSURE OF FIRST ASPECT OF THE INVENTION

The present inventors, as a result of a repeated intensive investigation for attaining the above-mentioned purposes, have found that a compound or a polymer having a specified structure has a photo-curability or thermosetting property, whereby, the above-mentioned purposes can be attained, and the present invention was completed.

That is, the present invention provides a compound represented by formula (1). Further, there is provided the compound characterized in that a group including a reactive functional group is a group including an alicyclic epoxy group.

Still further, there is provided the compound characterized in that the aliphatic hydrocarbon group substituted by a group including a reactive functional group is a group represented by formula (2) or (3). Also, there is provided a polymer of the compound. In addition, there is provided a process for the preparation of a compound represented by formula (1) which comprises allowing to react a compound having a hydroxyl group represented by formulae (4-1) or (4-2) with a compound represented by formula (5). Hereinafter, the present invention is illustrated in detail.

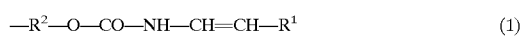

(in the formula, $R^1$ represents a hydrogen atom, an aromatic hydrocarbon group, or a saturated or unsaturated aliphatic hydrocarbon group, $R^2$ represents an aliphatic hydrocarbon group substituted by a group including a reactive functional group)

(in the formula, $R^4$ and $R^5$ represent a hydrogen atom, a methyl group or ethyl group, respectively, "m" is an integer of 4–8, and "n" is an integer of 1–10)

(in the formula, $R^4$ and $R^5$ represent a hydrogen atom, a methyl group or ethyl group, respectively, "m" is an integer of 4–8, and "n" is an integer of 1–10)

(in the formula, $R^1$ represents a hydrogen atom, an aromatic hydrocarbon group, or a saturated or unsaturated aliphatic hydrocarbon group).

BRIEF DESCRIPTION OF DRAWINGS

FIG. 2 is an IR chart of a polymer (polymer A) from the compound A obtained in Example 4.

BEST MODE FOR CARRYING OUT THE FIRST ASPECT OF THE INVENTION

Figure 1:
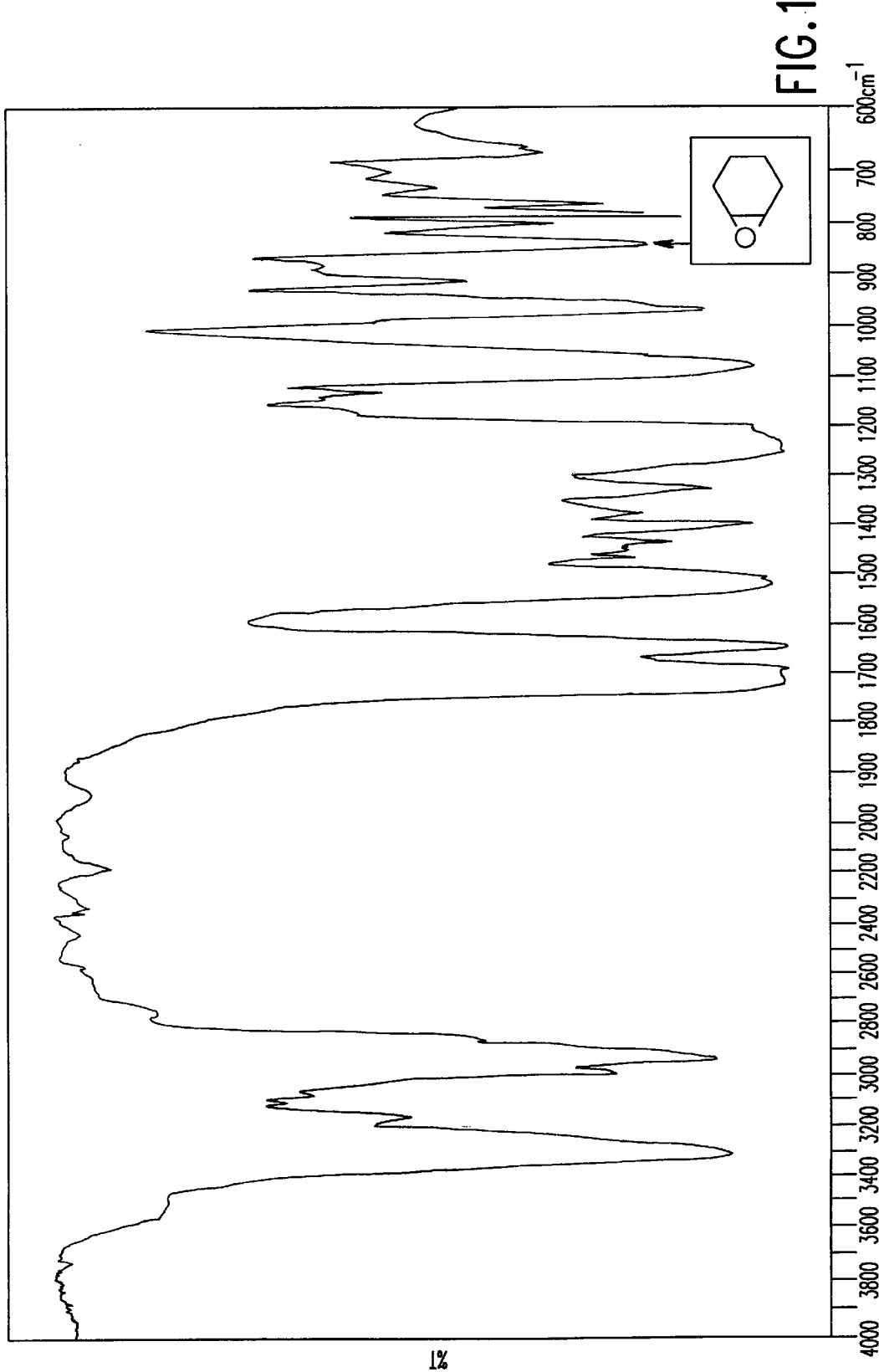
FIG. 1 is an IR chart of 3,4-epoxycyclohexylmethyl oxycarbonylvinylamine (compound A) obtained in Example 1.

In the compound represented by the formula (1) of the present invention, $R^1$ is preferably a hydrogen atom, an aromatic hydrocarbon group, or a saturated or unsaturated aliphatic hydrocarbon group.

In the case of the aromatic hydrocarbon group, a phenyl group and benzyl group are preferred. Further, in the case of the saturated aliphatic hydrocarbon group, an alkyl group having a carbon number of 1–10 is preferred. Still further, in the case of the unsaturated aliphatic hydrocarbon group, there are particularly preferred vinyl group, allyl group, and a (meth)acrylic group. Of those, particularly, $R^1$ is most preferably a hydrogen atom, methyl group, ethyl group, and phenyl group.

$R^2$ represents an aliphatic hydrocarbon group substituted by a group including a reactive functional group and, in particular, it is preferably a group represented by the above-mentioned formula (2) or (3). It is to be noted that in the formula (3), $R^4$ and $R^5$ are a hydrogen atom, a methyl group or ethyl group, respectively, "m" is preferably an integer of 4–8, and "n" is preferably an integer of 1–10.

The compound represented by the formula (1) can be prepared by allowing to react, for example, a compound having a hydroxyl group represented by formula (4-1) or (4-2) with a compound represented by the formula (5). Herein, the compound having a hydroxyl group represented by the formula (4-1) is 3,4-epoxycyclohexylmethyl alcohol. Also, the compound having a hydroxyl group represented by the formula (4-2) is a lactone polymer which can be prepared by polymerizing 1–10 mol of a lactone with 3,4-epoxycyclohexylmethyl alcohol. The compound having a hydroxyl group represented by the formula (4-2) can be prepared by a ring-opening polymerization of, specifically, ε-caprolactone using an initiator which is a compound having an active hydrogen such as the compound (4-1) which is an alcohol.

As the lactone, in addition to ε-caprolactone, valerolactone may be also polymerized solely or copolymerized with ε-caprolactone, etc.

On the other hand, the compound represented by the formula (5) can be prepared by allowing to react an aqueous solution of alkali or alkali earth metal salts typified by, for example, sodium azide which is a metal azide with $R^1$—CH=CH—COCl which is an acid chloride. As the $R^1$, the same group $R^1$ is employed as in the compound represented by the formula (1) which is a desired product.

In the reaction of the metal azide with the acid chloride, the acid chloride is preferably allowed to react in reaction ratio of 0.01–1.5 mol based on 1 mol of the metal azide. The reaction is conducted by adding dropwise a solution of the acid chloride into an aqueous solution of the metal azide. Solvents for the acid chloride are not particularly limited, and there are preferred ketones such as acetone and methylethyl ketone. Also, although dropwise addition of the metal azide into an aqueous solution can be conducted at temperature of from −78 to 100° C., it is preferably conducted at a room temperature or lower temperatures in view of stability of the metal azide.

The compound represented by the formula (1) is usually prepared by allowing to react generally 0.5–10.0 mol of the compound having a hydroxyl group represented by the formula (4-1) or (4-2) with 1 mol of a compound represented by the formula (5).

The reaction temperature is preferably 0 to 150° C. in view of a relationship between a stability of the compound represented by the formula (5) and the reaction temperature. In the reaction, a catalyst can be employed. As the preferred catalysts, there can be exemplified a tertiary amine such as triethyl amine and dimethylbenzyl amine, a quaternary amine such as tetraethyl ammonium chloride, and phosphines such as triphenyl phosphine.

The compound represented by the formula (1) can be polymerized solely or copolymerized with other compound having a polymerizable unsaturated group owing to a carbon—carbon double bond in the molecule. As polymerization processes, there are exemplified a solution polymerization, an emulsion polymerization, a suspension polymerization, and a sedimentation polymerization, and a solution radical polymerization is most convenient.

Copolymerizable monomer is not particularly limited, if it is a compound having a polymerizable unsaturated group, and there are exemplified the following monomers. Specifically, as alkyl(meth)acrylates, there are methyl(meth)acrylates, ethyl(meth)acrylates, propyl(meth)acrylates, butyl(meth)acrylates, pentyl(meth)acrylates, and hexyl (meth)acrylates, and the like. Further, as alkyl(meth)acrylates having hydroxyl group, there are 2-hydroxyethyl (meth)acrylates, hydroxypropyl(meth)acrylates, hydroxybutyl(meth)acrylates, and a caprolactone-modified 2-hydroxyethyl(meth)acrylates, and the like. Still further, as other (meth)acrylates, there are exemplified methoxydiethylene glycol(meth)acrylate, ethoxydiethyleneglycol(meth) acrylate, isooctyloxydiethyleneglycol(meth)acrylate, phenoxytriethylene glycol(meth)acrylate, methoxytriethyleneglycol(meth)acrylate, and methoxypolyethyleneglycol(meth)acrylate, and the like, and further, as other monomers, there are styrenes, and the like.

As a polymerization initiator to be employed for obtaining the polymer of the present invention, there can be employed initiators which are usually employed for polymerization of the compound having a polymerizable unsaturated group.

As specific examples, there can be exemplified peroxide-based compounds such as lauroyl peroxide, di-t-butyl peroxide, bis(4-t-butylcyclohexyl)peroxydicarbonate, t-butylperoxy(2-ethylhexanoate), methylethylketone peroxide, benzoyl peroxide, and cumenhydroperoxide, azo-based compounds such as 2,2-azobis isobutylonitrile and 2,2'-azobis-(2,4-dimethylvaleronitrile).

Further, the peroxide-based compounds and azo-based compounds may be also employed by mixing with each other.

In polymerization reaction, a polymerization solvent can be employed, and it is not particularly limited, if it can dissolve the monomers and the polymers. For example, there are employed aromatic hydrocarbons such as benzene, toluene, and xylene, alcohols such as methylalcohol, ethylalcohol, and 2-propanol, ketones such as acetone, methylethylketone, and methyl isobutylketone, ethers such as diethylether, dibutylether, and dioxane, acetates such as ethyl acetate, isobutyl acetate, and ethyleneglycol monoalkylether acetates, diethyleneglycol monoalkylether acetates, amides such as dimethylformamide and dimethylacetamide, halogenated hydrocarbons such as carbon tetrachloride and chloroform, and the like. The solvents may be employed solely or in combination. A number average molecular weight in polymers or copolymers obtained usually ranges from 5,000 to 500,000, preferably 10,000 to 80,000 based on a standard polystyrene with a GPC.

The compound (1) of the present invention, a homopolymer thereof, and a copolymer thereof are mixed with other resins, ring-opening addition catalysts for an epoxide, monomers or oligomers for dilution, photo-initiators, and other additives to obtain a curable resin composition which can be employed as a resist by photo-curing or thermally-curing.

In the other resins which can be mixed with the compound (1) of the present invention or the polymer thereof, an acid value preferably ranges from 50 to 150 KOHmg/g. In the case that the acid value is less than 50 KOHmg/g, it is difficult to sufficiently remove an uncured resin composition by a diluted aqueous alkali solution and, in the case that the acid value exceeds 150 KOH mg/g, moisture resistance and electric properties become occasionally poor in a cured layer. Further, a weight average molecular weight in the resin to be mixed preferably ranges from 5,000 to 150,000. However, the range is different according to uses, and in uses such as a solder resist or etching resist, etc. in which the thickness of a coating layer is not more than 30 $\mu$m, a weight average molecular weight preferably ranges from 10,000 to 40,000 in view of a requirement of an excellent developability. Still further, in uses such as a printing plate, etc. in which the thickness of a coating layer is 100 $\mu$m or so, a weight average molecular weight preferably ranges from 100,000 to 150,000 or so because of attaching importance to sensitivity. In the case that the weight average molecular weight exceeds 150,000, developability remarkably lowers, and there is occasionally also caused a problem that storage stability becomes poor.

As ring-opening addition catalysts for an epoxide capable of mixing with the compound (1) of the present invention and polymer thereof, there can be exemplified a tertiary amine such as dimethylbenzyl amine, triethyl amine, tetramethyl ethylenediamine, and tri-n-octyl amine, a quaternary amine such as tetramethyl ammonium chloride, tetramethyl ammonium bromide, and tetrabutyl ammonium bromide, an alkyl urea such as tetramethyl urea, an alkyl guanidine such as tetramethyl guanidine, and phosphines such as triphenyl phosphine, and salts thereof. Those may be employed solely or in combination of two or more kinds. These catalysts are preferably employed in an amount of 0.01–10% by weight, more preferably 0.5–3.0% by weight based on the compound of the formula (1) which is an epoxy compound, or the (co)polymer thereof. In the case of less than 0.01% by weight, a catalytic effect is low and, in the case that the amount exceeding 10% by weight is added, curability becomes poor.

As monomers or oligomers for dilution capable of mixing with the compound (1) of the present invention and polymer thereof, there can be exemplified a compound having a radical polymerizable double bond typified by an acrylate or methacrylate compound, a vinyl aromatic compound, and an amide-based unsaturated compound, and the like.

As the acrylate or methacrylate, there can be exemplified alkyl(meth)acrylates such as methyl(meth)acrylate, ethyl (meth)acrylate, propyl(meth)acrylate, butyl(meth)acrylate, pentyl(meth)acrylate, and hexyl(meth)acrylate, alkyl(meth) acrylates having hydroxyl group such as 2-hydroxyethyl (meth)acrylates, hydroxypropyl(meth)acrylates, hydroxybutyl(meth)acrylates, and caprolactone-modified 2-hydroxyethyl(meth)acrylates, alkoxy(meth)acrylates such as methoxydiethyleneglycol(meth)acrylate, ethoxydiethyleneglycol (meth)acrylate, isooctyloxydiethyleneglycol (meth)acrylate, phenoxytriethyleneglycol(meth)acrylate, methoxytriethyleneglycol (meth)acrylate, and methoxypolyeneglycol#400-(meth)acrylate, bifunctional (meth)acrylates such as 1,6-hexanediol di(meth)acrylate and neopentylglycol di(meth)acrylate, trifunctional (meth) acrylates such as trimethylolpropane tri(meth)acrylate, and polyfunctional (meth)acrylates such as dipentaerythritol hexaacrylate, and the like. Further, as the vinyl aromatic compound, there can be exemplified styrene, vinyltoluene, and $\alpha$-methylstyrene, and the like. Still further, as the amide-based unsaturated compound, there can be exemplified acryl amide and methacryl amide, and the like.

On the other hand, as the oligomers, there can be exemplified (meth)acrylates of a polyester polyol, (meth)acrylates of a polyether polyol, an adduct of a polyepoxide to (meth) acrylic acid, and a resin in which hydroxy(meth)acrylate is introduced into a polyol through a polyisocyanate, and the like.

The monomers or oligomers for dilution capable of mixing preferably range from 0 to 300 parts by weight, particularly, from 10 to 100 parts by weight based on 1 part by weight of the compound of the present invention or the polymer of the present invention. In the case that the monomers or oligomers for dilution exceed 300 parts by weight, developability occasionally lowers.

As the photo-polymerization initiator capable of mixing with the compound (1) of the present invention or the polymer thereof, there can be exemplified benzophenone, acetophenone, benzyl, benzyldimethyl ketone, benzoin, benzoin methylether, benzoin ethylether, benzoin isopropylether, dimethoxy acetophenone, dimethoxyphenyl acetophenone, diethoxy acetophenone, and diphenyldisulfide, and the like, and which may be employed solely or in mixing of two or more kinds. The photo-polymerization initiator can be employed together with, for example, a tertiary amine which is an agent for giving a synergetic effect by which there is accelerated conversion of absorbed photo-energy to a free radical for initiating polymerization. It is to be noted that in the case of curing the compound of the present invention and the polymer thereof by irradiation of an electronic beam, the photo-polymerization initiator may also be not mixed.

As the other additives capable of being mixed with the compound (1) of the present invention or the polymer thereof, there can be optionally exemplified an inhibitor for a thermal polymerization, a surface active agent, a photo-absorbent, a thixotropic agent, a dye, and a pigment, and the like.

For employing the compound of the present invention and the polymer thereof, a curable resin is coated as a thin layer on a base material, and then cured. As a method for forming the thin layer, there are employed spraying, brushing, a roll coating, a curtain coating, an electro-deposition coating, and an electrostatic coating, and the like. Further, in the case that it is employed as a liquid resist or dry film, it is cured by light after coating a curable resin composition on a base material. As "light", there can be employed a high pressure mercury lamp, an ultraviolet ray, an EB, and a laser beam, and the like. Still further, in the case that it is employed as one component in a liquid resist, it is also thermally cured. Curing can be conducted at conditions of 100–200° C., and 1–90 minutes.

Although curing is preferably conducted in an atmosphere of an inert gas, it can be also conducted in air atmosphere.

EXAMPLES OF FIRST ASPECT OF THE INVENTION

Hereinafter, although the present invention is specifically illustrated by Examples, the present invention is not limited by those. It is to be noted that "%" represents "% by weight" except particularly showing.

Example 1
Synthesis of 3,4-epoxycyclohexyl methyloxycarbonyl vinylamine)

A separable flask having capacity of 100 ml equipped with an agitator, a thermometer, a regulator for reflux, a dropwise funnel, and a tube for supplying nitrogen was charged 20 ml of aqueous solution containing 2.8 mol/liter of sodium azide, followed by adding dropwise 20 ml of acetone solution containing 2.5 mol/liter of acrylic chloride at 0° C. over 10 minutes and by aging for 2 hours. Successively, there were added 3.84 g of 3,4-epoxycyclohexylmethylalcohol ("ETHB" manufactured by Daicel Chemical Industries, Ltd.) and 5 ml of triethylamine, followed by allowing to react at 70° C. for 12 hours. From a reaction liquid obtained, 3,4-epoxycyclohexylmethyl oxycarbonylvinylamine (hereinafter, referred to as Compound A) was obtained. Yield was 72%.

There are shown the measurement results of IR and NMR in relation to the Compound A.

(1) IR: 3300 (N—H), 2930 (—$CH_2$—, a cycloaliphatic methylene), 1710 (C=O), 1640 (vinyl group), 850 (epoxy group) $cm^{-1}$.

(2) $^1$H-NMR ($CDCl_3$): δ=0.7–2.5 (m, 7H), 3.17 (s, 2H), 3.91 (dd, 2H, J=2.6 Hz, 6.4 Hz), 4.26 (d, 1H, J=8.2 Hz), 4.49 (d, 1H, J=15.4 Hz), 6.69 (dd, 1H, J=8.2 Hz, 15.4 Hz), 7.1 (br. s, 1H).

(3) $^{13}$C-NMR ($CDCl_3$): δ=20.86 (t), 22.76 (d), 23.46 (d), 24.38 (t), 26.82 (t), 27.96 (t), 29.58 (t), 32.29 (t), 50.98 (d), 51.53 (d), 52.34 (d), 69.08 (t), 93.03 (t), 130.03 (d), 153.81 (s).

Compound A

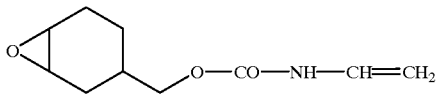

Examples 2 and 3

The same operations were followed as in the Example 1, except that acrylic chloride in the Example 1 was changed to methacrylic chloride to obtain Compound B (Example 2). Also, likewise, the same operations were followed as in the Example 1, except that acrylic chloride in the Example 1 was changed to phenylacrylic chloride to obtain Compound C (Example 3). It was identified by measurements with IR and NMR that the Compounds B and C are compounds shown by the following structures. Yield of the Compound B was 83%, and yield of the Compound C was 74%.

Compound B

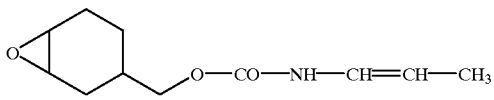

Compound C

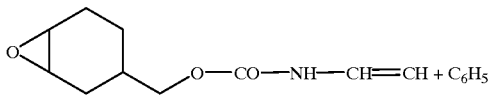

Example 4
Synthesis of a polymer from the Compound A

Under an atmosphere of nitrogen, there were charged 10 ml of benzene, 24.6 mg of 2,2'-azobisisobutylonitrile ("AIBN" manufactured by Nihon Hydrazine, Ltd.), and 985 mg of the Compound A in a sealed tube. Subsequently, temperature was elevated to 70° C., and a polymerization reaction was conducted for 24 hours. After the reaction, a polymer (hereinafter, referred to as Polymer A) was isolated using a benzene/hexane system. As a result, yield was 72%.

There were conducted an IR measurement, an NMR analysis, and a GPC measurement in relation to the Polymer A obtained, and it was identified that the Polymer A is a polymer of the Compound A.

(1) IR (KBr): 3320 (N—H), 2930 (a cycloaliphatic methylene), 1700 (C=O), 810 (epoxy group) $cm^{-1}$.

(2) $^1$H-NMR ($CDCl_3$): δ=0.8–2.5 (m, 10H), 3.23 (s, 2H), 3.86 (s, 1H), 5.5 (gr, s, 1H).

(3) $^{13}$C-NMR ($CDCl_3$): δ=21.07 (t), 22.91 (d), 23.62 (d), 24.54 (t), 26.87 (t), 28.17 (t), 29.74 (t), 32.45 (t), 45.78 (d), 51.03 (d), 51.58 (d), 52.39 (d), 68.70 (t), 156.19 (s).

GPC (based on Polystyrene); Number average molecular weight (Mn)=39,790, Molecular weight distribution (Mw/Mn)=1.67

Examples 5 and 6
Synthesis of a polymer from the Compound B or C

The same operations were followed as in the Example 4, except that the Compound A in the Example 4 was changed to the Compound B or C. Polymer B was obtained from the Compound B, and Polymer C was obtained from the Compound C.

It was identified that the Polymers B and C are a polymer of the Compounds B and C, respectively, from IR, NMR, and GPC analyses in relation to the Polymers B and C.

Reference Example
Synthesis of a solution of a resin having carboxylic groups Into a 2L-separable flask equipped with an agitator, a thermometer, a regulator for reflux, a dropwise funnel, a tube for supplying nitrogen gas, there were charged 300 g of dipropyleneglycol monomethylether ("MFDG" manufactured by Nihon Nyukazai, Ltd.), and 12.0 g of t-butylperoxy 2-ethylhexanoate ("Perbutyl O" manufactured by Nihon Yushi, Ltd.) and, after temperature was elevated to 95° C., there were added dropwise 172 g of methacrylic acid, 126 g of methylmethacrylate, 9.5 g of 2,2'-azobisisobutylonitrile ("ABN-E" manufactured by Nihon Hydrazine Kogyo, Ltd.), and 200 g of MFDG over 3 hours. After the dropwise addition, aging was conducted for 4 hours to prepare a main polymer having carboxylic groups. Subsequently, there were added 202 g of epoxycyclohexyl methylacrylate ("Cyclomer A200" manufactured by Daicel Chemical Industries, Ltd.), 2 g of triphenylphosphine, and 1.0 g of methylhydroquinone to allow to react with the main polymer at 100° C. for 10 hours. Reaction was conducted in a mixed gases atmosphere of air/nitrogen. By the reaction, there was obtained Resin solution D having an acid value of 100 KOHmg/g, double bond equivalent (the resin weight per 1 mol of unsaturated groups) of 450, and a weight average molecular weight of 20,000.

Example 7
Evaluation of a photo-curable resin

The Compound A obtained in the Example 1, the Polymers A, B, and C obtained in the Examples 4–6, and the Resin solution D obtained in the Reference Example were mixed with dipentaerythritol hexaacrylate (DPHA) which is a monomer for dilution, Phthalocyanine Green which is a dye, and 2-methyl-1-[4-(methylthio)phenyl]-2-morfolinopropane-1 ("Irugacure 907" manufactured by Ciba-Geigy, AG) which is an initiator by mixing proportion as shown in Table-1 to prepare a photo-curable resin composition by which an evaluation for a solder resist was conducted.

The solder resists obtained in the Example were coated on a base plate on which a pattern is formed in the thickness of 20–30 μm with a bar-coater, followed by drying at 80° C. for 20 minutes with an air-circulation dryer. And then, a negative film was closely contacted, and there was irradiated a beam having 1000 mJ/cm². Further, developing was conducted with 1% sodium carbonate aqueous solution, and a coating layer obtained was dried at 150° C. for 30 minutes in an air-circulation oven to obtain a solder resist layer. There were evaluated developing time (min), sensitivity, adhesion, heat resistance in soldering, and hydrolysis resistance in the solder resists in the Examples.

Results are shown in Table 1.

Measured items and methods for measuring (1) Developing time: As the developing time, there was measured a developing time in 1% sodium aqueous solution, and it was evaluated according to the following standards. It is to be noted that "soluble in a diluted aqueous alkali solution" means that the developing time is less than 20 seconds. o: less than 20 seconds, ▲: developable within 20–60 seconds, x: required exceeding 60 seconds.

(2) Sensitivity: It was evaluated with a Step Tablet manufactured by Kodak, Co.

(3) Adhesion: Peeling test using a cellophane tape was conducted in relation to the resist layer obtained according to JIS D0202. o: 100/100, ▲: 50/100–99/100, x: 0/100–49/100.

(4) Heat resistance in a solder: Appearances in a solder resist layer were visually evaluated after immersed in a solder bath at 260° C. for 20 seconds. o: No abnormality in a coating layer, ▲: Blisters and peeling were slightly observed in a coating layer, x: Blisters and peeling were observed in a coating layer.

(5) Hydrolysis resistance: After immersed in warm water at 40° C. for 24 hours, appearances in a coating layer were visually evaluated for judgement. o: Quite no change, ▲: Glossiness was slightly lost in a coating layer, x: Glossiness was lost.

TABLE 1

| | (part by weight) | | | |
| --- | --- | --- | --- | --- |
| | Example 1 | Example 2 | Example 3 | Example 4 |
| Polymer A | 100 | | | |
| Polymer B | | 100 | | |
| Polymer C | | | 100 | |
| Resin solution D | 100 | 100 | 100 | 100 |
| Compound A | | | | 20 |
| DPHA | 40 | 40 | 40 | 20 |
| Phthalocyanine Green | 2 | 2 | 2 | 2 |
| Irugacure 907 | 7 | 7 | 7 | 7 |
| Evaluation Result | | | | |
| Developing time (min) | o | o | o | o |
| Sensitivity | 7 | 7 | 7 | 7 |
| Adhesion | o | o | o | o |
| Heat resistance in a solder | o | o | o | o |
| Hydrolysis resistance | o | o | o | o |

According to the present invention, there can be provided a novel compound which is exceedingly useful, and which can be employed for a curable resin composition. The novel compound and a polymer (a multi-functional epoxy resin) therefrom can form a cured layer by coating on the surface of a metal, and then by irradiating a radiation ray such as an ultraviolet ray and an electronic beam. According to the present invention, there can be obtained a multi-functional monomer or a polymer therefrom which provides a curable resin composition which is excellent in adhesion of a coating layer, heat resistance in a solder, and resistance in a weak aqueous alkali, etc.

TECHNICAL FIELD OF SECOND ASPECT OF THE INVENTION

Second aspect of the invention relates to an active energy ray-curable type resist resin composition containing reactive functional groups and the uses. In more detail, it relates to an active energy ray-curable type resist resin composition which can be readily cured by heating or photo-irradiation, and it can be developed by an alkali.

BACKGROUND ART OF SECOND ASPECT OF THE INVENTION

Heretofore, as an active energy ray-curable type unsaturated resin composition, there have been developed a variety of compositions and these are widely utilized in fields of coatings, composite materials, and electronic parts, and the like. Further, it has been recently tried to develop a resin composition which is mainly composed of a vinyl resin as one of the active energy ray-curable type unsaturated resin composition. Still further, as a composition which is mainly composed of a vinyl resin, there is presently known a product obtained by a reaction of a vinyl resin having a high acid value with a vinyl compound having an aliphatic epoxy group.

However, in a coating layer formed from the composition, there are not sufficient an adhesion and water resistance, and it does not show properties to be sufficiently satisfied in practical uses.

DISCLOSURE OF SECOND ASPECT OF THE INVENTION

The present inventor, as a result of an intensive investigation for solving the above-mentioned problems, has found that there can be solved the above-mentioned problems by an active energy ray-curable type unsaturated resin composition in which a reaction product of an unsaturated compound which has a specified structure containing a cycloaliphatic epoxy group with an unsaturated resin having acid groups is diluted by an organic solvent and a polymerizable vinyl monomer, and attained a completion of the present invention.

That is, the present invention provides an active energy ray-curable type unsaturated resin composition which comprises mixing a reaction product of an unsaturated compound containing an alicyclic epoxy group represented by formula (6) with an unsaturated resin containing acid groups, with a diluent.

Further, there is provided the active energy ray-curable type unsaturated resin composition, wherein the unsaturated resin containing acid groups is an acryl-based resin containing acid groups. Still further, there is provided an alkali developable and active energy ray-curable type resist resin composition which comprises the active energy ray-curable type unsaturated resin composition. Hereinafter, the present invention is illustrated in detail.

$$R^2\text{—}O\text{—}CO\text{—}NH\text{—}CH\text{=}CH\text{—}R^1 \quad (6)$$

(in the formula, $R^1$ represents a hydrogen atom, an aromatic hydrocarbon group, or a saturated or unsaturated aliphatic hydrocarbon group, $R^2$ represents formula (2) or (3)),

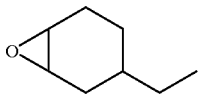

(2)

(3)

(in the formula, $R^4$ and $R^5$ represent a hydrogen atom, a methyl group or ethyl group, respectively, "m" is an integer of 4–8, and "n" is an integer of 1–10).

BEST MODE FOR CONDUCTING THE SECOND ASPECT OF THE INVENTION UNSATURATED COMPOUND CONTAINING AN ALICYCLIC EPOXY GROUP

The unsaturated compound containing an alicyclic epoxy group to be employed in the present invention is the compound represented by the above-mentioned formula (6) and, of the compound of the first aspect of the invention represented by the formula (1), it is a compound having the same $R^2$, and it is prepared by the same method for the preparation, and it has the same structural formula as in the compound represented by the above-mentioned formula (2) or (3).

The compound represented by the formula (6) to be employed in the present invention can be also employed as a copolymer by copolymerizing owing to a carbon-carbon double bond in the molecule with one or more kinds of monomers employed in the acryl-based resin containing acid groups which is described below.

UNSATURATED RESIN CONTAINING ACID GROUPS

As the unsaturated resin containing acid groups to be employed in the present invention, if it is a resin containing at least one of unsaturated groups and acid groups in the molecule, it may be employed and, for example, there can be exemplified an ethylenic unsaturated acid (co)polymer, an acrylic resin containing acid groups, a modified unsaturated monocarboxylic acid, a polyester resin containing acid groups, a bisphenol A type resin containing acid groups, a novolak resin containing acid groups, a polyamide acid, and a polyimide containing acid groups. Of those, there are preferred the ethylenic unsaturated acid (co)polymer and the acryl-based resin containing acid groups. Because a method for the preparation is simple, and resin properties can be readily controlled.

As the above-mentioned ethylenic unsaturated acid (co) polymer, there can be exemplified a (co)polymer of maleic anhydride, maleic acid, fumaric acid, and itaconic acid, etc.

As the above-mentioned acryl-based resin containing acid groups, there can be exemplified a (co)polymer of an acryl-based monomer containing acid group such as acryl-based compounds, for example, acrylic acid, methacrylic acid, carboxymethyl, (meth)acrylate, 2-carboxyethyl(meth) acrylate, 2-carboxypropyl(meth)acrylate, 2-carboxypropyl (meth)acrylate, crotonic acid, and β-carboxyethyl(meth) acrylate, and further an adduct of ε-caprolactone to (meth) acrylic acid. Further, as the acryl-based resin containing acid groups, there can be also employed a copolymer in which the above-mentioned acryl-based monomer is employed as an essential component, and there are copolymerized together one kind or more kinds of monomers selected from the following compounds.

As the monomers to be employed herein, there can be exemplified (i) esters of a (meth)acrylic acid, for example, a methyl(meth)acrylate, an ethyl(meth)acrylate, a propyl (meth)acrylate, a butyl(meth)acrylate, a 2-ethylhexyl(meth) acrylate, a stearyl(meth)acrylate, a hydroxyethyl(meth) acrylate, and a hydroxypropyl(meth)acrylate, and the like, (ii) an aromatic vinyl compound, for example, styrene, α-methylstyrene, vinyltoluene, and p-chlorostyrene, and the like, (iii) an amide-based unsaturated compound, for example, a (meth)acrylamide, diacetone acrylamide, N-methylolacrylamide, and N-butoxymethylacrylamide, and the like, (iv) a polyolefin-based compound, for example, butadiene, isoprene, and chloroprene, and the like, (v) and others, for example, a (meth)acrylonitrile, methylisopropenyl ketone, vinyl acetate, vinyl propionate, and vinyl pivarate, and the like.

As the above-mentioned modified unsaturated monocarboxylic acid, if it is a modified unsaturated monocarboxylic acid containing an unsaturated group and carboxylic group, in which a chain is extended between the unsaturated group and carboxylic acid, it is not particularly limited and, for example, there can be exemplified an unsaturated monocarboxylic acid having ester bond such as a lactone-modified compound in which terminal hydroxyl group is modified by an acid anhydride, and a modified unsaturated monocarboxylic acid having ether bond, and the like.

It is to be noted that the unsaturated resin containing acid groups to be employed in the present invention is a resin which is a reaction product into which unsaturated groups are introduced, and which is obtained by allowing to react all or partial acid groups in the unsaturated resin with all or partial epoxy groups derived from the unsaturated compound containing an alicyclic epoxy group. Accordingly, it is required that unsaturated groups which are capable of being cured by an active energy ray are introduced into a reaction product obtained, an acid value in the compound is preferably not less than 15 KOHmg/g, and more preferably 40–500 KOHmg/g.

REACTION OF THE UNSATURATED COMPOUND CONTAINING AN ALICYCLIC EPOXY GROUP WITH THE UNSATURATED RESIN CONTAINING ACID GROUPS

The unsaturated compound containing an alicyclic epoxy group represented by the formula (6) is preferably allowed to react with the unsaturated resin containing acid groups in an amount ranging in 1.08–5 mol of carboxylic groups in the unsaturated resin containing acid groups based on 1 mol of the unsaturated compound containing an alicyclic epoxy group. Because there sufficiently proceeds a ring-opening addition reaction of epoxy groups with acid groups in the range. It is to be noted that in 100 parts by weight of the unsaturated resin containing alicyclic epoxy groups which is allowed to react with the unsaturated resin containing acid groups in the present invention, there can be also employed together an unsaturated compound containing an aliphatic epoxy group such as glycidylmethacrylate, β-methylglycidyl methacrylate, and allylglycidylether, and further, any one of other alicyclic epoxy compounds containing an unsaturated group described hereinafter in a range of 0–90% by weight. As $R^7$ in the compounds described hereinafter, there are exemplified linear or branched alkylene groups, that is, methylene, ethylene, propylene, trimethylene, tetramethylene, ethylethylene, pentamethylene, and hexamethylene groups, and the like. Also, as $R^8$, there are exemplified methylene, ethylene, propylene, trimethylene, tetramethylene, ethylethylene, pentamethylene, and hexamethylene, polymethylene, phenylene, 1,4-cyclohexylene, and p-xylene groups, and the like.

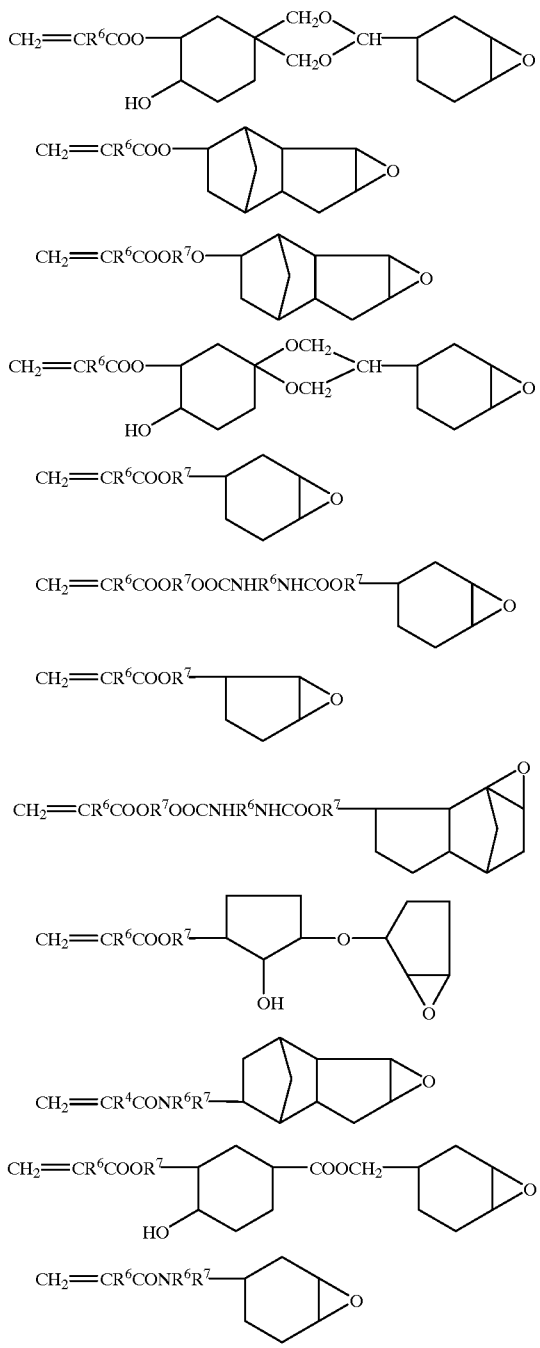

-continued (in the respective general formulae, $R^6$ represents a hydrogen atom or a methyl group, $R^7$ represents a divalent aliphatic saturated hydrocarbon group having a carbon number of 1–6, $R^8$ represents a divalent hydrocarbon group having a carbon number of 1–10, and "m" is an integer of 1–10).

The unsaturated compound containing an alicyclic epoxy group represented by the formula (6) to be employed in the present invention is added into a solution of an alcohol-based, an ester-based, an aromatic hydrocarbon-based, and an aliphatic hydrocarbon-based inert organic solvent containing the unsaturated resin containing acid groups, followed by allowing to react by maintaining both compounds at 20–120° C. for 1–7 hours.

Herein, in the case that the unsaturated aliphatic resin containing acid groups is an acryl-based resin containing acid groups, it can be allowed to react in reaction conditions of 20–120° C. for approximately 1–5 hours.

In a reaction product obtained, the number of unsaturated groups ranges in 0.2–4.0 pieces, preferably 0.7–3.5 pieces of based on 1000 of a molecular weight. In the case of less than 0.2 piece, curability becomes insufficient in a coating layer, and adhesion and water resistance, and the like for a substrate become occasionally poor. On the other hand, in the case that the number of the unsaturated groups is more than 4.0 pieces, it is unpreferably anxious that viscosity increases and gelation is caused during the addition reaction with the acryl-based resin containing acid groups and during a storage of the composition for a long time of period. Also, in the reaction product obtained, a number average molecular weight preferably ranges in 1,000–100,000, and more preferably 3,000–70,000. In the case of less than 1,000, water resistance becomes poor in a cured layer and, in the case that the molecular weight is more than 100,000, viscosity increases and handling becomes inconvenient, unpreferably resulting in that coatability also becomes worse and there becomes poor adhesion to a water-resistible substrate. And also, in the reaction product obtained, an acid value is preferably not more than 300 KOHmg/g. In the case that the acid value is more than 300 KOHmg/g, unpreferably, water resistance becomes occasionally poor in the layer.

AN ACTIVE ENERGY RAY-CURABLE TYPE UNSATURATED RESIN COMPOSITION

By mixing a diluent in the above-mentioned reaction product to be employed in the present invention, there can be obtained an active energy ray-curable type unsaturated resin composition according to uses and properties of a coating layer to be required. As the diluent to be mixed in the composition of the present invention, there can be employed an organic solvent and a polymerizable compound. The organic solvent is not limited in the kind, and there is preferred a solvent having a boiling point higher than the reaction temperature, and further, which can dissolve raw materials and the product. For example, there can be exemplified alcohols such as ethyl alcohol, propyl alcohol, isopropyl alcohol, and butanol, glycols such as ethylene glycol, propylene glycol, and dipropylene glycol, glycol ethers such as methylcellosolve, propylene glycol monomethylether, and dipropylene glycol monomethylether, glycol esters such as ethylene glycol diacetate and dipropylene glycol monomethylether acetate, and a mixed solution thereof. The organic solvent is not particularly limited in the amount to be employed. It can be appropriately selected by a coating method, and it can be diluted as having a viscosity according to respective coating methods.

In the case that a dipcoater, and the like are employed, the concentration of solid content in resins is preferably 1–40% by weight and, in the case that a roll coater and a curtain coater are employed, it is preferably 20–60% by weight or so.

As the polymerizable compound, there can be likewise employed the compounds exemplified as "a polymer or an oligomer for dilution" in the first aspect of the present invention and, further, there can be exemplified a polyolefin-based compound and a polymerizable prepolymer, and the like. Herein, as the polyolefin-based compound, an alkali-soluble resin is preferred.

For example, there can be exemplified a PVA, an acrylic resin containing acid groups, and polyolefines containing phenol groups, and the like. Further, as the polymerizable polymer, there can be exemplified, for example, a resin containing polymerizable unsaturated groups which can be modified to a water-soluble resin, for example, a resin in which a hydroxyalkyl(meth)acrylate is introduced into a polyol having carboxylic groups through a polyisocyanate compound, a resin containing polymerizable unsaturated groups, for example, a (meth)acrylate of a polyester polyol, a (meth)acrylate of a polyether polyol, a (meth)acrylate of an acryl polyol, an adduct of a polyepoxide to (meth)acrylic acid, and a resin in which a hydroxyalkyl(meth)acrylate is introduced into a polyol through a polyisocyanate compound, and the like. As other diluents, there can be exemplified an adduct of a monomer containing hydroxyl group to a monoisocyanate such as butyl isocyanate and phenylisocyanate, a monomer containing adilidine group, and a vinyl monomer containing phosphorus, and the like.

The polymerizable compound is preferably mixed in a range of less than 100 parts by weight, more preferably not more than 50 parts by weight based on 100 parts by weight of resinous solid components in the active energy ray-curable type resin composition. Because, hardness, solvent resistance, and alkali resistance, and the like are occasionally poor in a resin coating layer.

In the active energy ray-curable type resin composition of the present invention, there can be employed together a synergetic agent in order to accelerate conversion of absorbed photo-energy to polymerization radical groups, for example, such as the ring-opening addition catalysts for an epoxide exemplified in the first aspect of the invention. Those may be employed solely, or in combination of two or more kinds. The catalysts are preferably employed in 0.01–20% by weight, more preferably 0.1–10% by weight based on the compound of the formula (6) or a (co)polymer thereof. In the case of less than 0.01% by weight, an effect as a catalyst is low and, in the case of adding an amount exceeding 20% by weight, curability becomes poor. It is to be noted that a photo-polymerization initiator may be not added in the case that the composition of the present invention is cured by irradiation of an electronic beam.

As other agents for mixing, there can be added a photo-polymerization initiator. As the photo-polymerization initiator, there can be likewise employed the photo-polymerization initiator exemplified in the first aspect of the invention. Those may be employed solely, or in combination of two or more kinds. Further, the photo-polymerization initiator is preferably mixed in a range of 0.1–10% by weight based on the active energy ray-curable type resin composition. Still further, in the composition of the present invention, there can be optionally mixed pigments and dyes, and the like within an extent in which curability by an active energy ray is not deteriorated.

USES

The active energy ray-curable type resin composition of the present invention is particularly useful for coatings, printing inks, photo-resists, solder-resists, printing materials, adhesives, and pressure-sensitive adhesives, and the like. In the composition of the present invention, a coating layer can be formed by a method in which coating is conducted on wooden materials, papers, inorganic materials, plastics, and metals (zinc, iron, copper, and aluminum, and the like) with a coating machine such as, for example, a natural roll coater, a reverse roll coater, a gravure roll coater, a screen printer, a curtain coater, a dip coater, an air spray, an airless spray, a bar-coater, a knife coater, a spin coater, and a brush and dipping coating machine, and the like, followed by curing the coating layer through irradiating the active energy ray such as an electronic beam or ultra-violet ray. Thickness in the above-described coating layer is preferably not more than 2000 $\mu$m after dried, and particularly 0.1–1000 $\mu$m. In the case that the thickness in the coating layer exceeds 2000 $\mu$m, curability becomes unpreferably poor at an inside of the coating layer.

Further, as the electronic beam accelerator in order to discharge the active energy ray, there can be employed a Cockcroft type, a Cockcroft Walton type, a Vin de Graph type, a co-transformer type, a transformer type, an insulating core transformer type, a Dynamitron type, a linear filament type, a broad beam type, an area beam type, a cathode electrode type, and a high frequency type one, and the like. Herein, although an irradiation amount of the electronic beam, if there is given a necessary dose by which a coating layer is cured, is not particularly limited, there is irradiated a dose of approximately 0.5–20 mega-rad (Mrad) at approximately 100–2000 keV. Irradiation of the electronic beam is preferably conducted in an atmosphere of an inert gas. Still further, as irradiating means of the ultraviolet ray in order to discharge the active energy ray, there can be exemplified a mercury lamp, a high pressure mercury lamp, a xenon lamp, a carbon arc lamp, a metal halide lamp, and sun light, and the like. Irradiation of the ultraviolet ray is preferably conducted in an atmosphere of air or an inert gas. In the case that irradiation is conducted in an atmosphere of air, particularly, the high pressure mercury lamp is preferably employed as an irradiating source. In addition, although the irradiation conditions are different according to an amount absorbed into the photo-polymerization initiator, irradiation is conducted within several minutes, usually within a range of 1 second-20 minutes with a beam having 3000–4500 Å.

EXAMPLES OF SECOND ASPECT OF INVENTION

Hereinafter, although the present invention is specifically illustrated by Examples, the present invention is not limited by those. It is to be noted that "part" represents "part by weight" except particularly showing.

Synthesis Example 1

Into a separable flask equipped with an agitator, a thermometer, a regulator for reflux, a dropwise funnel, and a tube for supplying nitrogen, there were charged 55 parts of propyleneglycol monomethylether ("MMPG" manufactured by Daicel Chemical, Ltd.), 3.3 parts of t-butylperoxy-2-ethylhexanoate ("Perbutyl O" manufactured by Nihon Yushi, Ltd.), followed by adding dropwise 18 parts of acrylic acid, 30 parts of styrene, 35 parts of butylacrylate, 3 parts of 2,2-azobis(2-methylbutylonitrile) ("ABN-E" manufactured by Nihon Hydrazine Kogyo, Ltd.), and 8 parts of "MMPG" over 3 hours after heating a temperature to 95° C. After the dropwise addition, aging was conducted for 4 hours to prepare a main polymer having carboxylic groups.

Subsequently, there were added 42 parts of a compound (A) described hereinafter, 4 parts of triphenylphosphine, and 0.2 part of methylhydroquinone into the main polymer solution, followed by allowing to react at 100° C. for 10 hours. Reaction was conducted in an atmosphere of a mixed gas composed of air/nitrogen. By the reaction, there was obtained a resinous solution having an acid value of 20 KOHmg/g, a double bond equivalent (g weight of a resin per 1 mol of unsaturated groups) of 590, and a weight average molecular weight of 20,000.

Synthesis Example 2

The same operations were followed as in the Synthesis Example 1, except that a compound (B) described hereinafter was employed in place of the compound (A) in the Synthesis Example 1. By the operations, there was obtained a resinous solution having an acid value of 1 KOHmg/g, a double bond equivalent (g weight of a resin per 1 mol of unsaturated groups) of 590, and a weight average molecular weight of 20,000.

Synthesis Example 3

Into a separable flask equipped with an agitator, a thermometer, a regulator for reflux, a dropwise funnel, and a tube for supplying nitrogen, there were charged 90 parts of butyl alcohol and 4 parts of "Perbutyl O", followed by adding dropwise 23.4 parts of acrylic acid, 40 parts of butylmethacrylate, 35 parts of butylacrylate, 3.5 parts of "ABN-E", and 8 parts of methylisobutyl ketone over 3 hours after heating a temperature to 95° C. After the dropwise addition, aging was conducted for 4 hours to prepare a main polymer having carboxylic groups.

Subsequently, there were added 64 parts of the compound (A), 10 parts of triphenylphosphine, and 0.26 part of methylhydroquinone into the solution, followed by allowing to react at 100° C. for 10 hours. Reaction was conducted in an atmosphere of a mixed gas composed of air/nitrogen. By the reaction, there was obtained a resin solution having an acid value of 0 KOHmg/g, a double bond equivalent (g weight of a resin per 1 mol of unsaturated groups) of 500, and a weight average molecular weight of 17,000.

Synthesis Example 4

Into a separable flask equipped with an agitator, a thermometer, a regulator for reflux, a dropwise funnel, and a tube for supplying nitrogen, there were charged 90 parts of butyl alcohol and 4 parts of t-butylperoxy-2-ethylhexanoate (Perbutyl O manufactured by Nihon Yushi, Ltd.), followed by adding dropwise 23.4 parts of acrylic acid, 40 parts of butylmethacrylate, 35 parts of butylacrylate, 3.5 parts of "ABN-E", and 8 parts of methylisobutyl ketone over 3 hours after heating a temperature to 95° C. After the dropwise addition, aging was conducted for 4 hours to prepare a main polymer having carboxylic groups.

Subsequently, there were added 32 parts of the compound (A), 32 parts of a compound (C) ("CYM M100" manufactured by Daicel Chemical, Ltd.) described hereinafter, 10 parts of triphenylphosphine, and 0.26 part of methylhydroquinone into the solution, followed by allowing to react at 100° C. for 10 hours.

Reaction was conducted in an atmosphere of a mixed gas composed of air/nitrogen. By the reaction, there was obtained a resin solution having an acid value of 0 KOHmg/g, a double bond equivalent (g weight of a resin per 1 mol of unsaturated groups) of 500, and a weight average molecular weight of 17,000.

Synthesis Example 5

Into a separable flask equipped with an agitator, a thermometer, a regulator for reflux, a dropwise funnel, and a tube for supplying nitrogen, there were charged 100 parts of "MMPG", 4 parts of "Perbutyl O", followed by adding dropwise 45 parts of acrylic acid, 20 parts of methylmethacrylate, 35 parts of butylacrylate, 3.5 parts of "ABN-E", and 10 parts of "MMPG" over 3 hours after heating a temperature to 95° C. After the dropwise addition, aging was conducted for 4 hours to prepare a main polymer having carboxylic groups.

Subsequently, there were added 65 parts of the compound (A), 6.5 parts of triphenylphosphine, and 0.27 part of methylhydroquinone into the solution, followed by allowing to react at 100° C. for 10 hours. Reaction was conducted in an atmosphere of a mixed gas composed of air/nitrogen. By the reaction, there was obtained a resin solution having an acid value of 100 KOHmg/g, a double bond equivalent (g weight of a resin per 1 mol of unsaturated groups) of 500, and a weight average molecular weight of 17,000.

Synthesis Example 6

Into a separable flask equipped with an agitator, a thermometer, a regulator for reflux, a dropwise funnel, and a tube for supplying nitrogen, there were charged 100 parts of "MMPG" and 4 parts of "Perbutyl O", followed by adding dropwise 45 parts of acrylic acid, 20 parts of methylmethacrylate, 35 parts of butylacrylate, 3.5 parts of "ABN-E", and 10 parts of "MMPG" over 3 hours after heating a temperature to 95° C. After the dropwise addition, aging was conducted for 4 hours to prepare a main polymer having carboxylic groups.

Subsequently, there were added 33 parts of the compound (A), 32 parts of the compound (C), 6.5 parts of triphenylphosphine, and 0.27 part of methylhydroquinone into the solution, followed by allowing to react at 100° C. for 10 hours. Reaction was conducted in an atmosphere of a mixed gas composed of air/nitrogen. By the reaction, there was obtained a resin solution having an acid value of 100 KOHmg/g, a double bond equivalent (g weight of a resin per 1 mol of unsaturated groups) of 500, and a weight average molecular weight of 17,000.

Synthesis Example 7

Into a separable flask equipped with an agitator, a thermometer, a regulator for reflux, a dropwise funnel, and a tube for supplying nitrogen, there were charged 55 parts of "MMPG", 3.3 parts of "Perbutyl O", followed by adding dropwise 18 parts of acrylic acid, 30 parts of styrene, 35 parts of butylacrylate, 3 parts of "ABN-E", and 8 parts of "MMPG" over 3 hours after heating a temperature to 95° C. After the dropwise addition, aging was conducted for 4 hours to prepare a main polymer having carboxylic groups. Subsequently, there were added 30 parts of glycidylmethacrylate, 3 parts of triphenylphosphine, and 0.2 part of methylhydroquinone into the solution, followed by allowing to react at 100° C. for 10 hours. Reaction was conducted in an atmosphere of a mixed gas composed of air/nitrogen. By the reaction, there was obtained a resin solution having an acid value of 20 KoHmg/g, a double bond equivalent (g weight of a resin per 1 mol of unsaturated groups) of 530, and a weight average molecular weight of 18,000.

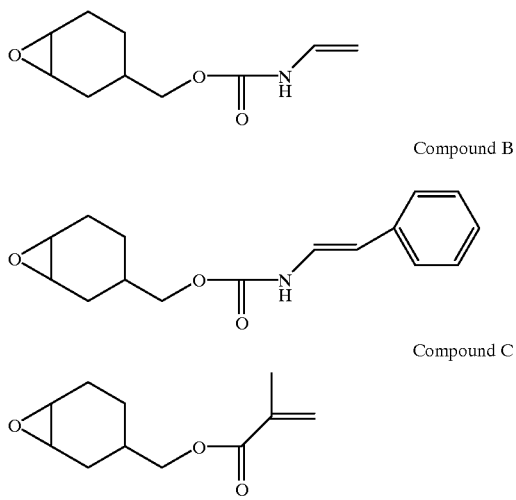

Example 1

10 parts by weight of α-hydroxyisobutylphenone was added into 300 parts by weight of the solution in the Synthesis Example 1 to prepare a solution, and the solution was coated on an aluminum plate with a bar-coater, followed by allowing to cure through irradiation of a UV for 5 seconds with a high pressure mercury lamp of 120 W/cm after drying at 80° C. for 15 minutes.

Thickness of coating layer was approximately 20 μm. Also, there were measured adhesion and water resistance in the coating layer. Results are shown in Table 2.

Example 2

There were added 100 parts by weight of a compound (D) described below which is a vinyl monomer ("Aronix M5700" manufactured by Toa-Gosei, Ltd.) and 20 parts by weight of tripropyleneglycol diacrylate into 300 parts by weight of the solution in the Synthesis Example 1 to prepare a solution, followed by removing MMPG in the solution by reducing pressure while supplying air after heating to 100° C. Further, there was added 10 parts by weight of α-hydroxyisobutylphenone. Composition was coated on an aluminum plate with a bar-coater, followed by allowing to cure through irradiation with a high pressure mercury lamp of 120 W/cm for 5 seconds. Thickness of coating layer was 20 μm. There were measured adhesion and water resistance in the coating layer.

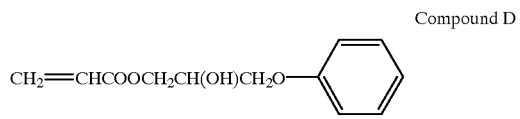

Example 3

There were added 106 parts by weight of "Aronix M5700" and 22 parts by weight of tripropyleneglycol diacrylate into 312 parts by weight of the solution in the Synthesis Example 2.

Solvent was likewise removed as in the Example 2, and there was added 17 parts by weight of α-hydroxyisobutylphenone.

Further, curing was conducted by the same methods as in the Example 2.

Example 4

There was added 6 parts by weight of α-hydroxyisobutyl phenone into 220 parts by weight of the solution in the Synthesis Example 3 to prepare a solution. The solution was coated on an aluminum plate with a bar-coater, followed by allowing to cure through irradiation of a UV for 2 seconds with a high pressure mercury lamp of 120 W/cm after drying at 80° C. for 15 minutes.

Thickness of coating layer was approximately 20 μm. There were measured adhesion and water resistance in the coating layer.

Example 5

There were added 50 parts by weight of "Aronix M5700" and 12 parts by weight of tripropyleneglycol diacrylate into 220 parts by weight of the solution in the Synthesis Example 4, followed by removing n-butanol and methylisobutyl ketone in the solution at reducing pressure while supplying air after heating to 100° C. Further, there was added 10 parts by weight of α-hydroxyisobutylphenone. Composition was coated on an aluminum plate with a bar-coater, followed by allowing to cure through irradiation for 2 seconds with a high pressure mercury lamp of 12 W/cm. Thickness of coating layer was 20 μm. There were measured adhesion and water resistance in the coating layer.

Comparative Example 1

After there was added 8 parts by weight of α-hydroxy isobutylphenone into 260 parts by weight of the solution in the Synthesis Example 7, the same test was conducted as in the Example 1.

Comparative Example 2

After there were added 80 parts by weight of "Aronix M5700" and 15 parts by weight of tripropyleneglycol diacrylate into 250 parts by weight of the solution in the Synthesis Example 7, and solvent was likewise removed as in the Example 2, there was added 13 parts by weight of α-hydroxyisobutylphenone. Further, curing was conducted by the same methods as in the Example 2.

TABLE 2

|  | Example | | | | | Comparative Example | |
| --- | --- | --- | --- | --- | --- | --- | --- |
|  | 1 | 2 | 3 | 4 | 5 | 1 | 2 |
| Curability | Excellent | Excellent | Excellent | Excellent | Excellent | Excellent | Excellent |
| Adhesion | 100/100 | 100/100 | 100/100 | 100/100 | 100/100 | 70/100 | 80/100 |
| Water resistance | 100/100 | 100/100 | 100/100 | 100/100 | 100/100 | 20/100 | 50/100 |

Example 6

There were added 50 parts by weight of tripropyleneglycol diacrylate, 50 parts by weight of 1,6-hexanediol diacrylate, and 50 parts by weight of trimethylolpropane triacrylate into 264 parts by weight of the solution in the Synthesis Example 3, followed by removing n-butanol which is a solvent in the solution at reducing pressure while supplying air after heating to 100° C.

Further, there was added 62 parts by weight of a Titanium White, followed by dispersing with a ball-mill to prepare a white-colored coating. The coating was coated on a plaster board having the thickness of 1.5 cm with a curtain-coater, followed by allowing to cure the coating layer through irradiation of an electronic beam of 7 mega-rad to prepare a plaster tile.

Thickness of the coating layer is approximately 100 μm.

Adhesive property to the plaster was excellent, and as a result of evaluation of outer appearance and adhesive property by sticking to a wall for 3 months, it was excellent without changing from an initial state.

Example 7

There were kneaded 198 parts by weight of the solution in the Synthesis Example 5, 20 parts by weight of a phenol novolak epoxy resin (an epoxy equivalent of 173), 5 parts by weight of α-hydroxyisobutylphenone, and 0.5 parts by weight of Phthalocyanin Green with a three-roll. Composition was employed as a solder resist ink for a printed circuit board. Subsequently, the ink was coated on a copper-through-hole printed circuit board by a screen-printing method. After drying (layer thickness of 15–20μ) at 70° C. for 10 minutes, a film on which a pattern is formed was closely attached to the board, followed by irradiating the dose of 1000 mJ/cm² with an ultra high pressure mercury lamp of 3 kw. Further, unexposed portions were removed with 1%-solution of sodium carbonate, followed by heating at 140° C. for 30 minutes to prepare a solder resist layer. The resist layer was excellent in heat resistance such as solder resistance, and chemical resistance to acids and alkalis. Results are shown in Table 3.

TABLE 3

|  | Example | |
| --- | --- | --- |
|  | 7 | 8 |
| Solder resistance | Excellent | Excellent |
| Acid resistance | 100/100 | 100/100 |
| Acid resistance | 100/100 | 100/100 |

Example 8

As a result that the same tests were conducted as in the Example 7 using the solution in the Synthesis Example 6, it was identified that an excellent resist layer can be formed. The resist layer was likewise excellent in heat resistance such as solder resistance, and chemical resistance to acids and alkalis as in the Example 7.

Measured Item (1) Curability: Curability was evaluated by a gel fraction. Dried coating layer was stripped from a base material, and it was extracted by acetone for 6 hours at a reflux temperature with a Soxhlet Extractor. Residual components from the coating layer were measured, and 90% and more was regarded excellent.

(2) Adhesion: 100 pieces of cross-hatched cuts were formed on a test piece with a interval of 1 mm according to JIS D-0202 Testing method, and those were peeled by a cellophane-made pressure sensitive tape. The number of the cross-hatched cuts which are not peeled off is shown as a numerator, and original number (100 pieces) of the cross-hatched cuts is shown as a denominator.

(3) Water resistance: Adhesion after immersion was measured to show as water resistance. Measurement was conducted as follows.

A coated plate was immersed in warm water of 50° C. for 1 day, and water was wiped from the coated plate. Further, after leaving as it is for 1 hour, the same test was conducted as in adhesion.

(4) Solder resistance: It was decided as 1 cycle that a test piece is floated on a solder bath of 260° C. for 10 seconds according to JIS C6481 Testing method, and 3 cycles were conducted to visually evaluate.

(5) Acid resistance: After immersed in 20%-hydrochloric acid at 30° C. for 1 hour, evaluation was conducted by a cross-hatched test.

(6) Alkali resistance: After immersed in 1%-sodium carbonate aqueous solution at 30° C. for 1 hour, evaluation was conducted by a cross-hatched test.

POSSIBILITY OF UTILIZATION IN INDUSTRY BY THE SECOND ASPECT OF THE INVENTION

In the active energy ray-curable type unsaturated resin composition of the present invention, there are introduced unsaturated groups which are curable by an active energy ray into a reaction product obtained by an addition reaction of an unsaturated compound containing an alicyclic epoxy group to acid groups derived from an unsaturated resin containing acid groups, which readily reacts depending upon a ring-opening polymerization reaction of epoxy groups. In a coating layer formed from the composition, since a chemical bond is a bond having a relatively large steric hindrance, which is formed by a chemical reaction of acid groups in the acrylic resin with the alicyclic epoxy groups, the coating layer is chemically stable to a substance which accelerates hydrolysis, for example, water and rain water, and the like. Accordingly, the active energy ray-curable type unsaturated resin composition of the present invention can provide a coating layer having a remarkable effect, for example, excellent durability such as water resistance, etc.

TECHNICAL FIELD OF THIRD ASPECT OF THE INVENTION

The third aspect of the invention relates to an active energy ray-polymerizable unsaturated resin composition and a liquid-state or powder-state active energy ray-curable resin composition composed of the resin composition which is excellent in chemical resistance, adhesion, and heat resistance.

BACKGROUND ART OF THIRD ASPECT OF THE INVENTION

Heretofore, as a photo-curable composition, there has been employed a composition in which inorganic fillers are mixed. The inorganic fillers are usually mixed in a large amount into a base material in order to obtain a photo-cured layer which is excellent in physical properties such as hardness and heat resistance. However, photo-transmittance in the resin composition lowers by the inorganic fillers mixed, or curability becomes worse in the layer, and further, the layer becomes brittle and porous, resulting in that there occasionally deteriorate mechanical properties, water resistance, adhesion, and chemical resistance, and the like in the layer. Further, a powder-state curable resin composition, in which there can be conducted a handling such as coating without the use of organic solvents, could be readily employed from a viewpoint of environmental protection in recent years.

DISCLOSURE OF THIRD ASPECT OF THE INVENTION

The present inventors, as a result of a repeated intensive investigation, have found that a resin composition can be modified into a powder-state, which is obtained by a reaction of a specified unsaturated compound containing an alicyclic epoxy group with colloidal silica in the presence of a metal chelate and/or a metal alkoxide, and a curable composition composed of the resin composition is excellent in curability by irradiation of an active energy ray and, further, a cured layer is excellent in mechanical properties, water resistance, chemical resistance, and adhesion, and the like, and the present invention was completed.

That is, the present invention provides an active energy ray-polymerizable unsaturated resin composition obtainable by allowing to react an unsaturated compound (E) containing an alicyclic epoxy group represented by formula (6) with a colloidal silica (F) in the presence of a metal chelate and/or metal alkoxide (hereinafter, referred to as "metal compound") (G).

Further, there is provided a powder-state active energy ray-polymerizable unsaturated resin composition obtained by removing a solvent from the active energy ray-polymerizable unsaturated resin composition. Still further, there is provided a liquid-state or powder-state active energy ray-curable composition which comprises the liquid-state or powder-state active energy ray-polymerizable unsaturated resin composition. Hereinafter, the present invention is illustrated in detail.

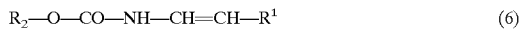

(in the formula, $R^1$ represents a hydrogen atom, an aromatic hydrocarbon group, or a saturated or unsaturated aliphatic hydrocarbon group, $R^2$ represents formula (2) or formula (3)),

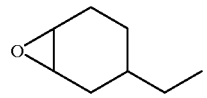

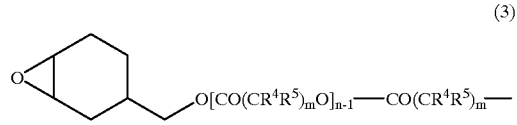

(in the formula, $R^4$ and $R^5$ represent a hydrogen atom, a methyl group or ethyl group, respectively, "m" is an integer of 4–8, and "n" is an integer of 1–10).

BEST MODE FOR CARRYING OUT THE THIRD ASPECT OF THE INVENTION UNSATURATED COMPOUND (E) CONTAINING AN ALICYCLIC EPOXY GROUP

The unsaturated compound (E) containing an alicyclic epoxy group to be employed in the present invention is a compound having one alicyclic epoxy group and at least one of the active energy ray-polymerizable unsaturated group in the molecule, and it is represented by the above-described formula (6) and, it is prepared by the same method and it has the same structural formula as in the compound in which $R^2$ is represented by the formula (2) or (3) in the compound represented by the formula (1) of the first aspect of the present invention. The unsaturated compound (E) containing an alicyclic epoxy group is characterized in that it contains one alicyclic epoxy group alone in the molecule. The reason why it is one depends upon that if it has two or more alicyclic epoxy groups, viscosity in a system occasionally increases and causes gelation in a reaction with the colloidal silica (F) in the presence of the metal compound (G).

The reason why the epoxy group is alicyclic depends upon that since a reaction of the epoxy group with a silanol group in the colloidal silica (F) is poor in a compound having an aliphatic epoxy group such as glycidyl group, the colloidal silica component does not sufficiently connect to a compound containing an unsaturated group, resulting in that there cannot be obtained a cured layer having excellent outer appearance and properties. Further, a carbon—carbon double bond in the unsaturated compound (E) containing an alicyclic epoxy group is an active energy ray-polymerizable unsaturated group, and it causes a polymerization reaction by being activated with an active energy ray such as visible light, an ultraviolet ray, and an electronic beam.

COLLOIDAL SILICA (F)

The colloidal silica (F) to be employed in the present invention means one in which there is dispersed silica powder having average particle size of 0.001–100 $\mu$m in an organic solvent.

As the colloidal silica to be employed in the present invention, there is preferred one in which there is dispersed silica powder having a silanol group at the surface and having average particle size of 0.005–0.1 $\mu$m in an organic solvent. By the presence of the silanol group, there can be readily conducted a reaction of the silanol group in the colloidal silica with the aliphatic epoxy group, and a curable composition obtained using this one is excellent also in curability by irradiation of an active energy ray, mechanical properties of a layer, water resistance, chemical resistance, and adhesion, etc. In the case that the average particle size is larger than 0.1 μm, a cured article occasionally causes whitening, and sedimentation stability occasionally lowers. On the other hand, in the case that the average particle size is smaller than 0.005 μm, viscosity increases in a composition obtained, unpreferably resulting in that handling becomes difficult.

As the organic solvent to be employed for the colloidal silica (F), if it can stably disperse the silica, it is can be employed without being particularly limited. There can be exemplified monovalent alcohols having a carbon number of 1–6 such as methyl alcohol, ethyl alcohol, n-propyl alcohol, iso-propyl alcohol, n-butyl alcohol, iso-butyl alcohol, sec-butyl alcohol, tert-butyl alcohol, n-pentyl alcohol, and n-heptyl alcohol, polyvalent alcohols such as ethylene glycol, diethylene glycol, propylene glycol, and dipropylene glycol, ethers such as ethyl cellosolve, butyl cellosolve, propylene glycol monomethylether, diethylene glycol monomethylether, ethylene glycol dimethylether, and diethylene glycol dimethylether, amides such as N,N-dimethylformamide, and nitriles such as acetonitrile, and the like. Further, organic solvents other than the above-described ones, for example, aromatic hydrocarbons, esters, and ketones, and the like, can be employed in combination.

METAL COMPOUND (G)

As the metal compound (G) to be employed in the present invention, there are metal chelates and metal alkoxides. As the metal chelates, there can be exemplified an aluminum chelate compound, a titanium chelate compound, or a zirconium chelate compound, and there can be also employed compounds described in JP-A-01129060 Official Gazette. Specifically, there can be exemplified diisopropoxyethyl acetoacetate aluminum, tris(ethylacetoacetate)aluminum, isopropoxy-bis(ethylacetoacetate)aluminum, monoacetylacetonate-bis(ethylacetoacetate)aluminum, tris(n-propylacetoacetate)aluminum, tris(isopropylacetoacetate)aluminum, tris(n-butylacetoacetate) aluminum, monoethylacetoacetate-bis(acetylacetonate) aluminum, tris(acetylacetonate)aluminum, tris(propionylacetonate)aluminum, acetylacetonate-bis(propionylacetonate)aluminum, diisopropoxy-bis(ethylacetoacetate)titanium, diisopropoxy-bis(acetylacetonate)titanium, tetrakis(n-propylacetoacetate) zirconium, tetrakis(acetylacetonate)zirconium, and tetrakis (ethylacetoacetate)zirconium, and the like. In the present invention, these may be employed solely or in combination.

As the metal alkoxides, there can be employed a compound in which an alkoxy group, preferably, an alkoxy group having a carbon number of 1–15 connects to metals such as aluminum, titanium, zirconium, sodium, potassium, calcium, and lithium.

The compounds may be associated. Specifically, there are preferably exemplified aluminum triisopropoxide, aluminum tri-sec-butoxide, aluminum tri-n-butoxide, titanium tetraisopropoxide, titanium tetra-n-butoxide, titanium tetraisobutoxide, titanium tetra-t-butoxide, zirconium tetraisopropoxide, zirconium tetra-n-propoxide, zirconium tetra-n-propoxide, zirconium tetraisobutoxide, zirconium tetra-n-butoxide, and zirconium tetra-t-butoxide, and the like. In the present invention, these may be employed solely or in combination of two or more kinds.

ACTIVE ENERGY RAY-POLYMERIZABLE UNSATURATED RESIN COMPOSITION

The active energy ray-polymerizable unsaturated resin composition of the present invention (hereinafter, referred to as "unsaturated resin composition") can be prepared by allowing to react the above-described unsaturated compound (E) containing an alicyclic epoxy group with the colloidal silica (F) in the presence of a metal compound (G).

The unsaturated compound (E) containing an alicyclic epoxy group can be mixed with the colloidal silica (F) in an appropriate ratio according to properties of coating layers to be required. There are usually mixed 20–80% by weight, preferably 20–70% by weight of the compound (E) and 80–20% by weight, preferably 80–30% by weight of the colloidal silica (F) based on the total amount of both solid components. In the case that the colloidal silica (F) is less than 20% by weight, properties such as hardness and heat resistance are not sufficient in a coating layer. On the other hand, in the case that the colloidal silica (F) exceeds 80% by weight, unpreferably, cracks are caused in a coating layer, and transparency become occasionally poor.

Further, "any one of other alicyclic epoxy compounds containing an unsaturated group" employed in the second aspect of the invention can be employed within a range of 99/1–1/99 parts by weight based on the compound (E).

The metal compound (G) is preferably mixed in a proportion of 0.01–10 parts by weight, particularly, 0.1–5 parts by weight based on 100 parts by weight of the total solid amount of the compound (E) and the colloidal silica (F). In the case of less than 0.01 part by weight, there is readily caused inferiority in curing, and in the case of exceeding 5 parts by weight, storage stability becomes poor, and physical properties in the coating layer are occasionally adversely affected.

The "unsaturated resin composition" of the present invention can be obtained by heating the compound (E) and the colloidal silica (F) at reaction temperature of 40–130° C. for 1–10 hours under the presence of the metal compound (G).

POWDER-STATE ACTIVE ENERGY RAY-POLYMERIZABLE UNSATURATED RESIN COMPOSITION

The powder-state active energy ray-polymerizable unsaturated resin composition of the present invention can be prepared by removing solvents from the above-described "unsaturated resin composition" according to a conventional method. Further, the powder-state active energy ray-curable resin composition (hereinafter, referred to as "curable composition") of the present invention is a composition in which curable resins and curable monomers shown below are mixed into the above-described "unsaturated resin composition". It is to be noted that in the "curable composition", the component of the colloidal silica (F) is preferably mixed as adjusted to a proportion of 20–80% by weight, preferably 30–80% by weight based on the total solid components in the "curable composition".

As a curable resin to be mixed, there can be employed conventionally known ones by appropriately selecting.

Specifically, there can be preferably employed oligomers such as an epoxy acryl-based oligomer, a polyester-based oligomer, a urethane acryl-based oligomer, an acryl-based oligomer, an oligoester acryl-based oligomer, an ether acryl-based oligomer, a butadiene-based oligomer, and an acryl-based oligomer containing a spirane ring. In the present invention, these preferably have at least one of an active energy ray-polymerizable unsaturated group on average, and a molecular weight is preferably 100–20,000.

Further, as a curable monomer to be mixed, there can be employed conventionally known ones by appropriately selecting.

Specifically, there can be exemplified a monofunctional vinyl monomer such as, for example, a methyl(meth) acrylate, an ethyl(meth)acrylate, a butyl(meth)acrylate, 2-ethylhexylacrylate, a 2-hydroxypropyl(meth)acrylate, a glycidyl(meth)acrylate, a (meth)acrylic acid, a (meth)acrylic amide, and styrene, a di- or tri-ester compound of a polyvalent alcohol such as ethyleneglycol, trimethylolpropane, glycerine, and pentaerythritol with a (meth)acrylic acid.

In the case that the "unsaturated resin composition" has a silanol group, curability in a resin and monomer to be mixed is improved by mixing compounds containing a functional group capable of reacting with the silanol group. As the compounds containing the functional group capable of reacting with the silanol group, there are compounds having (i) epoxy group, (ii) silanol group, (iii) hydrolyzable group which directly connects to silicone, (iv) hydroxyl group, and (v) isocyanate group, and the like. By mixing such the compounds, since there simultaneously occur a curing reaction by irradiation of an active energy ray and a curing reaction by heating, there is an effect that there are improved properties, etc. in a coating layer.

As the compounds having epoxy group (i), there can be exemplified a homopolymer of the above-described compound (E), a copolymer of the compound (E) with the above-described monomers except a (meth)acrylic acid, an alicyclic compound such as an alicyclic epoxy resin ("Chissonox 201" and "Chissonox 206" which are a product manufactured by Chisso, Ltd.), and further, the compounds described below. It is to be noted that although there can be also employed a compound having an aliphatic-type epoxy group, it is occasionally inferior in reactivity compared to the compound having an alicyclic epoxy group.

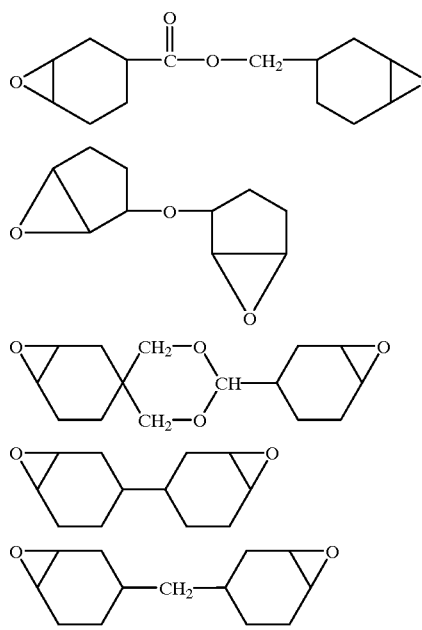

As the compounds having silanol group (ii) or the hydrolyzable group (iii) which directly connects to silicone, for example, an alkoxy group, an aryloxy group, and an acyloxy group, and the like, which have a silanol group and/or an alkoxysilane group, there can be preferably employed, for example, a polysiloxane-based monomer described in JP-A-62197423 Official Gazette, a monomer such as a vinyl monomer having an alkoxysilane group described in JP-A-63108049 Official Gazette, or a polymer containing the monomer as an essential component.

As the compounds having hydroxyl group (iv), there can be preferably employed, for example, a polyester-based polyol, a polyether-based polyol, an acryl-based polyol, a polysiloxane-based polyol, a polyurethane-based polyol, and a modified polyol therefrom. As the compounds having isocyanate group (v), there can be preferably employed, for example, a product in which polyisocyanates, for example, isophorone diisocyanate, and the like are allowed to react with the above-described polyols.

In the "curable composition" of the present invention, there can be optionally mixed organic solvents, for example, aromatic hydrocarbons, alcohols, ethers, esters, and ketones. By mixing the organic solvents, there can be adjusted viscosity, the thickness of a layer, stability, and fluidity, etc., resulting in becoming readily employed. Further, the water-soluble "curable composition" can be also obtained using the "unsaturated resin composition". Specifically, a resin capable of becoming water soluble is selected from the above-described resins. As the resin capable of becoming water soluble, there can be employed a conventionally known resin, specifically, unsaturated resins having a cationic or anionic group described in JP-B-77021526, JP-A-62262855, JP-A-64004671, and JP-A-64004672 Official Gazettes, more specifically, a resin in which a resin containing acid groups is neutralized by an amine, and a resin in which a resin containing acid groups is quartenerized by a compound having glycidyl group, a resin in which acid groups are neutralized by an alkali, a resin in which a compound having an unsaturated group and epoxy group is partially added to a resin containing acid groups, and then residual acid groups are neutralized by an amine, a resin quartenerized by a compound having glycidyl group, a resin in which a hydrophilic group is introduced using isocyanate group, and a resin having hydroxyl group and a polyether group, and the like. Still further, in the case that the "unsaturated resin composition" has silanol groups, there is selected a water-soluble compound from the above-described compounds containing a functional group capable of reacting with the silanol group. Specifically, there can be exemplified a silane compound containing mercaptan group, a silane compound containing amino group, and a silane compound containing hydroxyl group.

POWDER-STATE ACTIVE ENERGY RAY-CURABLE UNSATURATED RESIN COMPOSITION

In order to obtain the powder "curable composition" from the "unsaturated resin composition", there is selectively mixed a resin capable of being powdered from the above-described resins. In the case that the "unsaturated resin composition" has the silanol group, a compound which can be powdered is selected from the above-mentioned compounds containing a functional group capable of reacting with the silanol group.

In the "curable the composition" of the present invention, there can be optionally mixed coloring agents, dispersants, and agents for controlling fluidity, and the like. Also, the liquid-state or powder-state "curable composition" can be cured by irradiation of an active energy ray such as an electronic beam, an ultraviolet ray, and visible light. In the case that it is cured by irradiation of the ultraviolet ray or visible light, there can be mixed photo-polymerization initiators, sensitivity accelerators, and coloring agents into the composition.

As the photo-polymerization initiators, there can be employed the photo-polymerization initiators exemplified in the first aspect of the invention. These may be employed solely or in combination of two or more kinds. Further, the photo-polymerization initiators are preferably mixed in a range of 0.01–10% by weight based on the "curable composition".

A synergetic agent for accelerating a conversion of photo-energy absorbed to a free radical for initiation of polymerization can be mixed with the liquid-state or powder-state "curable composition" of the present invention, for example, a catalyst for addition by ring-opening of an epoxide can be employed together. As the catalyst for addition by ring-opening of an epoxide to be mixed, there can be employed the catalysts for addition by ring-opening of an epoxide exemplified in the first aspect of the invention. These may be employed solely or in combination of two or more kinds. These catalysts are preferably employed in a range of 0.01–10% by weight, preferably 0.1–5% by weight based on the "curable composition".

In the case of less than 0.01% by weight, a reaction rate of addition itself becomes slow, resulting in that it is practically unpreferred and, in the case of exceeding 10% by weight, physical properties are adversely affected in a coating layer. It is to be noted that in the case of curing the compound of the present invention and the composition thereof by irradiation of an electronic beam, the photo-polymerization initiator may also be not mixed.

As the coloring agents to be mixed into the liquid-state or powder-state "curable composition" of the present invention, there can be employed xanthone eocine and ketocoumarins, and the like. These may be employed solely or in combination of two or more kinds. These catalysts are preferably employed in a range of 0.01–70% by weight, preferably 0.1–50% by weight based on the "curable composition". In the case of less than 0.01% by weight, a reaction rate of addition itself becomes slow, resulting in that it is practically unpreferred and, in the case of exceeding 70% by weight, physical properties are adversely affected in a coating layer.

USES

The liquid-state or powder-state "curable composition" of the present invention can be applied for base materials such as woods, papers, inorganic materials, plastics, and metals.

Particularly, it is useful for coatings, printing inks, encapsulants, photo-resists, solder resists, plating resists, materials for printing negatives, and adhesives, and the like.

Of those, it is desirably employed as, particularly, encapsulants, protecting layers for electronic parts, and a variety of resist layers because of excellent chemical resistance, adhesion, and heat resistance. It depends upon that the liquid-state or powder-state "curable composition" of the present invention has high hardness and excellent chemical resistance in a coating layer. It is to be noted that if a water-based product from the "curable composition" is employed, it can be employed for a copper foil-laminated insulation board for a printed circuit as a negative type or positive type anionic electro-deposition coating, or a negative type or positive type cationic electro-deposition coating.

There can be employed a method for forming a coating layer using the "curable composition" of the present invention, thickness of the coating layer, an electronic beam accelerator for discharging the active energy ray, irradiation amount of the active energy ray, an irradiation source of an ultraviolet ray for discharging the active energy ray, and irradiation conditions, and the like in the same conditions as described in the second aspect of the invention.

EXAMPLES OF THIRD ASPECT OF THE INVENTION

Hereinafter, although the present invention is specifically illustrated by Examples, the present invention is not limited by those. It is to be noted that "part" and "%" represent "part by weight" and "%" by weight, except particularly showing.

Synthesis Example 1

Into a separable flask equipped with an agitator, a thermometer, a regulator for reflux, a dropwise funnel, and a tube for supplying nitrogen, there were charged 1000 parts of a silica sol ("IPA-ST" manufactured by Nissan Kagaku Kogyo, Ltd., which has solid content of 30% and average particle size of 0.01–0.02 $\mu$m), 150 parts of a compound (A) described hereinafter, 0.5 part of methylmethacrylate tris (acetylacetonate), and 0.04 part of aluminum methoxyhydroquinone, followed by allowing to react while agitating for 6 hours at 110° C. to obtain a resin solution having solid content of 39%.

Synthesis Example 2

The same operations were followed as in the Synthesis Example 1, except that 100 parts of the compound (A) and 50 parts of a compound (B) described hereinafter were employed in place of 150 parts of the compound (A) to obtain a resin solution.

Solid content was 39% in the resin solution obtained.

Synthesis Example 3

The same operations were followed as in the Synthesis Example 1, except that glycidylmethacrylate was employed in place of the compound (A) to obtain a resin solution. Solid content was 39% in the resin solution obtained.

Synthesis Example 4

The resin solution obtained in the Synthesis Example 1 was dried at 40° C. and reduced pressure to obtain a resin powder.

Synthesis Example 5

The resin solution obtained in the Synthesis Example 3 was dried at 40° C. and reduced pressure to obtain a resin powder.

Example 1

There were mixed 1150 parts of the resin solution obtained in the Synthesis Example 1 and 15 parts of α-hydroxyisobutyl phenone, followed by spray-coating onto the surface of an ABS (acrylonitrile-butadiene-styrene copolymer) plate so that the thickness of a layer becomes 20 $\mu$m in a dry state. After solvent was removed by heating at 70° C. for 10 minutes, exposure was conducted for 30 seconds from distance of 30 cm with a high pressure mercury lamp of 5 kw to obtain a layer. The layer was a continuous layer without defects such as cracks. Also, the layer was transparent and, moreover, it showed an excellent pencil hardness of 7H.

Comparative Example 1

The same operations were followed as in the Example 1, except that the resin solution in the Synthesis Example 3 was employed in place of the resin solution in the Synthesis Example 1 to obtain a layer. The layer did not form a continuous layer and, as a result of rubbing the surface by hand, it changed to a powder state and clung to the hand.

Example 2

There were mixed 1050 parts of the resin solution in the Synthesis Example 2, 150 parts of trimethylolpropane triacrylate, and 20 parts of benzoin ethylether, followed by spray-coating onto the surface of a zinc phosphate-treated steel plate so that the thickness of a layer becomes 30 $\mu$m in a dry state. After solvent was removed by heating at 70° C. for 10 minutes, exposure was conducted for 20 seconds from distance of 50 cm with a high pressure mercury lamp of 5 kw to obtain a layer. The layer was a continuous layer without defects such as cracks. The layer was transparent and, moreover, it showed pencil hardness of 8H, and cross-hatched adhesion was 100/100, which were excellent.

Comparative Example 2

The same operations were followed as in the Example 2, except that 1050 parts of the resin solution in the Synthesis Example 3 was employed in place of 1150 parts of the resin solution in the Synthesis Example 2 to obtain a layer. In the layer, there were caused fine cracks, and it was poor as a continuous layer. Also, the layer was not transparent and, cross-hatched adhesion was 0/100 and, as a result of pencil hardness, it was not able to be measured because the layer was stripped by scratching with a pencil.

Example 3

There was dispersed in a ball mill for 6 hours a mixture composed of 450 part of the resin powder in the Synthesis Example 4, 200 parts of an epoxy acryl oligomer [1 mol of "Epikote 828 (a Bis-A type glycidylether having an epoxy equivalent of 190 which is a liquid-state resin)" manufactured by Shell Kagaku, Ltd. is allowed to react with 2 mol of acrylic acid], 50 parts of 2-hydroxy-3-benzyloxypropyl acrylate, and 25 parts of a compound (C) described hereinafter. The mixture was supplied into a mild steel-made square cup having 1 cm$^2$, and exposure was conducted for 40 seconds from distance of 30 cm with a high pressure mercury lamp of 5 kw, followed by heating at 140° C. for 60 minutes to obtain a cast article. A thermocycle test was conducted in relation to the cast article. As a result, change was nothing before and after the thermocycle test.

Comparative Example 3

The same operations were followed as in the Synthesis Example 4, except that the resin powder in the Synthesis Example 5 was employed in place of the resin powder in the Synthesis Example 4 to obtain a cast article. A thermocycle test was conducted in relation to the cast article by the same methods as in the Example 4. As a result, cracks were caused in the cast article at period of 10 cycles.

Example 4

There were added 0.1 part of hydroquinone and 288 parts of acrylic acid into a resin solution in which 1100 parts of an epoxy resin ("Epikote 180S70 which is a cresol novolak epoxy resin having an epoxy equivalent of 210" manufactured by Shell Kagaku, Ltd.) is dissolved into 1045 parts of butyl cellosolve, followed by continuing a reaction while heating to 100° C. until an acid value becomes not more than 5. After cooled to 70° C., there were added 122 parts of thiodiglycol acid and 60 parts of acetic acid, and a reaction was conducted at 70° C. for 8 hours to obtain a resin solution having the solid content of 60% of a resin having acryloyl groups and hydroxyl groups. Subsequently, there was coated a mixture composed of 100 parts of the resin solution, 150 parts of the resin solution in the Synthesis Example 1, 15 parts of the compound (C), and 5 parts of benzoin ethylether onto a copper foil-laminated board having through holes so that there is formed a dried layer having the thickness of 30 $\mu$m. Subsequently, after solvent were removed by heating at 70° C. for 10 minutes, exposure was conducted with an irradiation dose of 300 mJ/cm$^2$ from distance of 50 cm using an ultra high pressure mercury lamp of 80 w/cm through a negative mask, followed by removing an unexposed layer by treating with a developer for a fixed period of time. Remained layer was heated at 140° C. for 30 minutes to form a resist layer pattern on the copper foil-laminated board. Results of properties in the layer obtained are shown in Table 4.

Example 5

Into a 2-liter separable flask equipped with a regulator, a dropwise funnel, and a tube for supplying nitrogen, there were charged 300 g of dipropyleneglycol monomethylether ("MFDG" manufactured by Nihon Nyukazai, Ltd.), 12.0 g of t-butylperoxy-2-ethylhexanoate ("Perbutyl O" manufactured by Nihon Yushi, Ltd.), and after a temperature was elevated to 95° C., there were added dropwise 172 g of methacrylic acid, 126 g of methylmethacrylate, 9.5 g of 2,2-azobis(2-methylbutylonitrile) ("ABN-E" manufactured by Nihon Hydrazine Kogyo, Ltd.), and 200 g of "MFDG" over 3 hours. After the dropwise addition, aging was conducted for 4 hours to prepare a main polymer having carboxylic groups. Subsequently, there were added 202 g of epoxycyclohexyl methylacrylate ("Cyclomer A200" manufactured by Daicel Chemical Industries, Ltd.), 2 g of triphenylphosphine, and 1.0 g of methylhydroquinone to allow to react with the main polymer at 100° C. for 10 hours. Reaction was conducted in a mixed gases atmosphere of air/nitrogen, whereby, there was obtained a resin solution having an acid value of 100 KoHmg/g, a double bond equivalent (the resin weight per 1 mol of unsaturated groups) of 450, and a weight average molecular weight of 20,000.

Subsequently, a resist layer pattern was likewise formed as in the Example 4 using a mixture composed of 100 parts of the resin solution, 150 parts of the resin solution in the Synthesis Example 1, 15 parts of the compound (C), and 5 parts of benzoin ethylether.

Comparative Example 4

The same operations were followed as in the Example 4, except that 150 parts of the resin solution in the Synthesis Example 1 was replaced with 130 parts of "Silica sol IPA-ST" to form a resist pattern layer.

Comparative Example 5

The same operations were followed as in the Example 4, except that the resin solution in the Synthesis Example 3 was employed by replacing with the resin solution in the Synthesis Example 1 to form a resist pattern layer. Table 4 collectively shows experimental results for properties of the layers in the Comparative Examples 4 and 5.

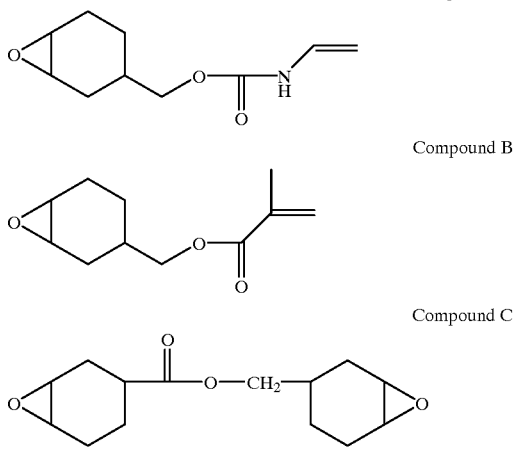

Compound A

Compound B

Compound C

TABLE 4

|  | Example 4 | Example 5 | Compative Example 6 | Compative Example 7 |
|---|---|---|---|---|
| Developability (90 seconds) | ⊚ | ⊚ | ⊚ | ⊚ |
| Developability (180 seconds) | ⊚ | ⊚ | ⊚ | ⊚ |
| Finger-touch dryability | O | ⊚ | O | O |
| Cross-hatched adhesion | 100/100 | 100/100 | 50/100 | 60/100 |
| Acid resistance | ⊚ | ⊚ | ▲ | ▲ |
| Solder resistance *1 | normal | normal | normal | normal |
| Solder resistance *2 | 4 | 4 | blister | blister |
| Solder resistance *3 | 100/100 | 100/100 | 0/100 | 0/100 |
| Immersion test for hot water resistance | 100/100 | 100/100 | 0/100 | 1/100 |

*1: Results of visual observation after 3 cycles in Solder resistance test
*2: Results of visual observation after 6 cycles in Solder resistance test
*3: Results of cross-hatched adhesion after 6 cycles in Solder resistance test

METHODS FOR MEASURING (1) Pencil hardness: It was conducted according to JIS K5400.

(2) Cross-hatched adhesion: 100 pieces of cross-cuts having an interval of 1 mm were formed on the surface of a layer with a cutter and, a cellophane tape was adhered to the cross-cuts, and adhesive conditions of the layer were observed after abruptly stripping. Results are shown by "the number of the cross-cuts remained/the number of the cross-cuts formed".

(3) Thermocycle test: 50 cycles were repeated to a cast article, in which 1 cycle is repetition of heating at 150° C. for 5 hours and cooling at −20° C. for 5 hours. Evaluation was visually conducted.

(4) Developability: It was conducted by spraying a developer (1.5 $Na_2CO_3$ aqueous solution) at 25° C. and spraying pressure of 2 kg/$cm_2$ for a fixed time (90 seconds and 180 seconds) onto a resist layer after exposed. Evaluations are shown by ⊚: being capable of developing through an inside of through holes, o: being capable of completely developing the surface of the board, ▼: there are caused defects in resist patterns such as portions which are incapable of developing the surface of a base plate or portions eroded or swelled by the developer, and x: being almost incapable developing.

(5) Finger-touch dryability: Film was closely adhered to a coating layer with a vacuum laminator, followed by visually observing after exposed. Evaluation standards are as follows, ⊚: the film is not quite stained by the coating layer, o: the film is slightly stained by the coating layer, x: the film is clearly stained by the coating layer.

(6) Acid resistance: It was visually observed after immersed in 1N $H_2SO_4$ at 60° C. for 1 hour, and it is shown by, ⊚: conditions do not quite change in coating layer, o: blistering and change of color are slightly observed in conditions of coating layer, ▼: change of color is clearly observed in conditions of coating layer, and x: coating layer is dissolved or peeled.

(7) Solder resistance (visual observation): Test pieces were floated according to JIS C6481 on a solder bath of 260° C. for 10 seconds as 1 cycle, and those were observed at third cycle and sixth cycle, followed by visually evaluating.

(8) Solder resistance (cross-hatched adhesion): Test pieces were floated according to JIS C6481 on a solder bath of 260° C. for 10 seconds as 1 cycle, and 100 pieces of cross cuts having an interval of 1 mm were formed on a coating layer with a cutter and, a cellophane tape was adhered to the cross cuts after sixth cycle, and adhesive conditions of the coating layer were observed after abruptly stripping. Results are shown by "the number of the cross-cuts remained/the number of the cross-cuts formed".

(9) Immersion test for boiled water resistance: After test pieces were immersed in hot water of 80–90° C. for 1 hour, and 100 pieces of cross cuts having an interval of 1 mm were formed on a layer with a cutter and, a cellophane tape was adhered to the cross cuts, and adhesive conditions of the layer were observed by abruptly stripping. Results are shown by "the number of the cross-cuts remained/the number of the cross-cuts formed".

POSSIBILITES OF UTILIZATION IN INDUSTRY BY THE THIRD ASPECT OF THE INVENTION

In the active energy ray-polymerizable unsaturated resin composition of the present invention, there can be readily conducted a reaction of the alicyclic epoxy group in the unsaturated compound (E) containing an alicyclic epoxy group with a silanol group in the colloidal silica (F) component in the presence of the metal compound (G) which is a catalyst. And, since a bond of the colloidal silica (F) with a polymerizable unsaturated group connects to the colloidal silica (F) through the alicyclic epoxy group, a layer composed of "curable composition" prepared using "resin composition" obtained is excellent in heat resistance and chemical resistance and, further, it is excellent in finishing and transparency, etc.

TECHNICAL FIELD OF FOURTH ASPECT OF THE INVENTION

The fourth aspect of the invention relates to a low temperature-curable resin composition and, in more detail, it relates to a low temperature-curable resin composition, which is a composition composed of a vinyl copolymer of a monomer having a polysiloxane structure with a vinyl monomer having a specified structure containing an oxirane group, a specified metal compound, and a specified compound containing at least two alicyclic oxirane groups, and which does not require water component in a curing reaction, and which is excellent in a low temperature curability and storage stability, and in which shrinkage is not caused because of a small difference in curability between the surface and inside, and which can provide a cured article having excellent weatherability and water resistance.

BACKGROUND ART OF FOURTH ASPECT OF THE INVENTION

In order to reduce energy costs, there has been intensively desired a development of a resin composition which is curable at low temperature. Heretofore, as a low temperature-curable resin composition, there has been mainly employed a two-liquid type resin composition such as a polyol/isocyanate system and an epoxy/polyamine system. However, in such the two-liquid type resin composition, since two components must be mixed immediately before employing, handling is troublesome. Further, in the case that an isocyanate is employed, there is a disadvantage of severe toxicity. On the other hand, although there is also known an active energy ray-curable-type and one-liquid type polymerizable unsaturated resin composition to be cured by an ultraviolet ray and an electronic beam, and the like, since an irradiation apparatus is indispensable, it is not regarded that operability is good. Still further, as a low temperature-curable resin composition which is a one-liquid type and does not require the irradiation apparatus, there is disclosed a composition in which an aluminum chelate compound is mixed in a vinyl polymer containing an alkoxysilane such as methacryloxypropyl trimethoxysilane, for example, in JP-A-60067553 Official Gazette.

However, since the composition in the above-described Official Gazette contains a silanol group alone which is generated by hydrolysis of the alkoxysilane group as a curable functional group, it requires a large amount of water in curing.

Also, physical properties in a cured article are not sufficient by the presence of a large amount of by-products such as alcohols which are generated in hydrolysis. Further, in the case that curing is conducted by moisture alone in air, because curing initiates at the surface, inner portions are not apt to be readily cured, whereby, there is a problem that shrinkage is apt to be caused in a cured article.

DISCLOSURE OF FOURTH ASPECT OF THE INVENTION

The present inventor, as a result of repeated intensive investigations for solving the problems in prior arts, has found that a silanol group and oxirane group which exist in a composition obtained act as a curable functional group by mixing a vinyl copolymer containing a specified polysiloxane-based macromonomer and a vinyl monomer having a specified vinyl monomer containing an oxirane group with a specified compound containing an alicyclic oxirane group and a specified organic metal compound and, whereby, the composition can be cured even at low temperatures of not more than 100° C., and shrinkage is slight because a curing reaction simultaneously progresses in the surface and inside portions of a cured article, and the present invention has been completed.

That is, the present invention provides a low temperature-curable resin composition characterized by containing the components (a), (b), and (c) described below.

(a) a vinyl copolymer having a number average molecular weight of 2,000–100,000 which is a copolymer of a polysiloxane-based macromonomer having a number average molecular weight of 400–50,000 containing at least two hydroxyl groups or alkoxyl groups in the molecule with a vinyl monomer containing oxirane group represented by formula (6) described below, and the macromonomer is obtained by allowing to react 70–99.999% by mol of a compound (H) represented by formula (7) described below with 30–0.001% by mol of a compound (J) represented by formula (8) described below, (b) a 6-coordinated organic aluminum chelate compound and/or an 8-coordinated organic zirconium chelate compound, and (c) a compound having a number average molecular weight of not more than 1,000 containing at least two alicyclic oxirane groups in the molecule. Hereinafter, the present invention is illustrated in detail.

(in the formula, $R^{11}$ represents an aliphatic hydrocarbon group having a carbon number of 1–8 or a phenyl group, and $R^{12}$, $R^{13}$, and $R^{14}$ represent an alkoxyl group having a carbon number of 1–4 or a hydroxyl group),

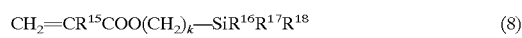

(in the formula, $R^{15}$ represents a hydrogen atom or a methyl group, $R^{16}$, $R^{17}$, and $R^{18}$ represent any one of a hydroxyl group, an alkoxyl group having a carbon number of 1–4, and an aliphatic hydrocarbon group having a carbon number of 1–8, "k" is an integer of 1–6, and all the $R^{16}$, $R^{17}$, and $R^{18}$ are not simultaneously an aliphatic hydrocarbon group having a carbon number of 1–8),

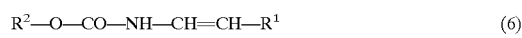

(in the formula, $R^1$ represents a hydrogen atom, an aromatic hydrocarbon group, or a saturated or unsaturated aliphatic hydrocarbon group, and $R^2$ represents formula (2) or (3)),

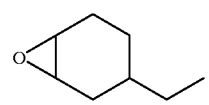

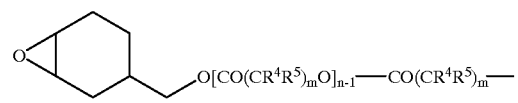

(in the formula, $R^4$ and $R^5$ represent a hydrogen atom, a methyl group or ethyl group, respectively, "m" represents an integer of 4–8, and "n" represents an integer of 1–10).

BEST MODE FOR CARRYING OUT THE FOURTH ASPECT OF THE INVENTION
COMPONENT (A)

The component (a) to be employed for the low temperature-curable resin composition of the present invention is a vinyl copolymer containing a polysiloxane-based macromonomer and a vinyl monomer containing oxirane group represented by the formula (6) as monomer components. In the component (a), a number average molecular weight ranges in 2,000–100,000 and, particularly, preferably in 4,000–50,000. In the case of less than 2,000, curability is poor and, on the other hand, in the case that the number average molecular weight is more than 100,000, there lower workability in coating and compatibility with the compound containing oxirane group which is the component (c).

POLYSILOXANE-BASED MACROMONOMER

The polysiloxane-based macromonomer which constitutes the component (a) is characterized in that it has a polysiloxane structure, and in which there connect to Si an alkoxyl group including an aliphatic hydrocarbon group, a phenyl group, hydroxyl group, an alkoxyl group, and an alkoxyl group containing a polymerizable carbon-carbon double bond, and the like, and which has at least two silanol groups or alkoxy silane groups in the molecule which connect to Si in the polysiloxane structure.

The polysiloxane-based macromonomer to be employed in the present invention can be prepared by a reaction of the compound (H) represented by the above-described formula (7) with the compound (J) represented by the above-described formula (8).

The compound (H) is represented by the above-described formula (7). In the formula, $R^{11}$ represents an aliphatic hydrocarbon group having a carbon number of 1–8 or a phenyl group, and there can be exemplified linear or branched groups such as methyl group, ethyl group, propyl group, butyl group, pentyl group, hexyl group, heptyl group, and octyl group. As the $R^{11}$, there are particularly preferred methyl group and phenyl group. $R^{12}$, $R^{13}$, and $R^{14}$ represent an alkoxyl group having a carbon number of 1–4 or a hydroxyl group, and which may be all identical or partially or wholly different from each other. As the alkoxyl group having a carbon number of 1–4, there can be exemplified linear or branched groups such as methoxy group, ethoxy group, propoxy group, and butoxy group. As the $R^{12}$, $R^{13}$, and $R^{14}$, there are particularly preferred methoxy group, ethoxy group, propoxy group, butoxy group, and hydroxyl group.

Specifically, as the compound (H), there can be exemplified methyl trimethoxysilane, phenyl trimethoxysilane, butyltrimethoxy silane, methyl triethoxysilane, methyl tributhoxysilane, phenyltrisilanol, and methyltrisilanol, etc. Of those, there are particularly preferred methyl trimethoxysilane, phenyl trimethoxysilane, and phenyltrisilanol. In the present invention, these can be employed one kind or two or more kinds of those.

The compound (J) is represented by the above-described formula (8). In the formula, $R^{15}$ represents a hydrogen atom or a methyl group, $R^{16}$, $R^{17}$, and $R^{18}$ represent any one of a hydroxyl group, an alkoxyl group having a carbon number of 1–4, and an aliphatic hydrocarbon group having a carbon number of 1–8, "k" represents an integer of 1–6. Although $R^{16}$, $R^{17}$, and $R^{18}$ may be all identical or partially or wholly different from each other, all of them must not be simultaneously an aliphatic hydrocarbon group having a carbon number of 1–8. Because it cannot connect to the compound (H). As the aliphatic hydrocarbon group having a carbon number of 1–8 and alkoxyl group having a carbon number of 1–4, there can be employed the same groups as exemplified in the compound (H). It is to be noted that as $R^{16}$, $R^{17}$, and $R^{18}$, there are preferred methoxy group, ethoxy group, and hydroxyl group and, as "n", a range of 2–4 is particularly preferred.

As the compound (J), there can be exemplified γ-methacryloxypropyl trimethoxysilane, γ-methacryloxypropyl triethoxysilane, γ-acryloxypropyl trimethoxysilane, γ-methacryloxybutyl triethoxysilane, and γ-acryloxypropyl trisilanol, and the like. Of those, there are particularly preferred γ-methacryloxypropyl trimethoxysilane, γ-methacryloxypropyl triethoxysilane, and γ-acryloxypropyl trisilanol. In the present invention, these can be employed one kind or two or more kinds thereof.

The polysiloxane-based macromonomer can be prepared by allowing to react after mixing the above-described compounds (H) and (J). As mixing ratio in the both compounds, the compound (H) ranges in 70–99.999% by mol, preferably 90–99.9% by mol, and more preferably 95–99% by mol, and the compound (J) ranges in 30–0.001% by mol, preferably 10–0.1% by mol, and more preferably 5–1% by mol. In the case that the compound (H) is less than 70% by mol, gelation is apt to be caused in a copolymerization reaction and, on the other hand, in the case of exceeding 99.999% by mol, there increases the amount of the polysiloxane which does not copolymerize, unpreferably resulting in that a resin solution becomes cloudy.

The reaction between the compounds (H) and (J) is a condensation accompanied by dehydration of hydroxyl groups in the both compounds or hydroxyl groups produced by hydrolysis of the alkoxyl group. In the case, there occurs not only the condensation accompanied by dehydration but also a condensation accompanied by removal of an alcohol depending upon reaction conditions. Although the reaction may be conducted without solvents, there are preferably employed organic solvents or water which can dissolve the compounds (H) and (J).

As the organic solvents to be employed, there can be exemplified hydrocarbon-based solvents such as heptane, toluene, xylene, octane, and mineral spirits, ester-based solvents such as ethyl acetate, n-butyl acetate, isobutyl acetate, methylcellosolve acetate, and butylcarbitol acetate, ketone-based solvents such as methylethyl ketone, methylisobutyl ketone, and diisobutyl ketone, alcohol-based solvents such as ethanol, isopropanol, n-butanol, sec-butanol, and isobutanol, ether-based solvents such as n-butylether, dioxane, ethylene glycol monomethylether, and ethylene glycol monoethylether, and the like. There can be employed one kind or two or more kinds of these. It is to be noted that in the case of employing in a solution state, the concentration of the compounds (H) and (J) is preferably not less than 5% by weight based on the total amount of both.

In the reaction between the compounds (H) and (J), temperature is 20–180° C. and, particularly, preferably 50–120° C.

Also, the reaction time is preferably 1–40 hours. In the reaction, a polymerization inhibitor can be optionally added.

The use of the polymerization inhibitor is effective for preventing polymerization of an unsaturated bond contained in the compound (J) during the reaction with the compound (H) and, for example, there can be employed hydroquinone and hydroquinone monomethylether, and the like. It is to be noted that in the preparation of the polysiloxane-based macromonomer, not more than 20% by mol of tetraalkoxy silane or dialkyl dialkoxy silane can be added based on 100% by mol of the total amount of the compounds (H) and (J) in a reaction system.

In the compounds (H) and (J) to be employed, in the case of a compound in which $R^{12}$, $R^{13}$, $R^{14}$, $R^{16}$, $R^{17}$, and $R^{18}$ are all hydroxyl group, condensation reaction accompanied by dehydration is preferably conducted while agitating and heating an organic solvent during the reaction. On the other hand, in the case of a compound in which either the compound (H) or (J) to be employed, or both have an alkoxyl group, hydrolysis is preferably conducted prior to the condensation. Usually, a hydrolysis reaction and a reaction for bonding are continuously conducted while heating and agitating in the presence of water and a catalyst. Although the use amount of water in the case is not particularly limited, there is preferred not less than 1 mol based on 1 mol of the alkoxyl group. In the case of being less than 1 mol, it is anxious that there lowers the reaction between the both compounds. There is most preferred a method in which excessively large amount of water is employed as a solvent.

In the hydrolysis reaction, even in the case of formation of a water-insoluble alcohol by the condensation, a reaction system can be homogenized by using water together with a water-soluble organic solvent. As the water-soluble organic solvent to be employed, there can be employed solvents such as an alcohol-based, ester-based, ether-based, and ketone-based one which are employed for dissolving the above-described compounds (H) and (J).

Further, in the hydrolysis reaction, catalysts can be employed. As the catalysts to be employed, there can be employed acid catalysts or alkali catalysts. As the acid catalysts, there can be exemplified hydrochloric acid, sulfuric acid, phosphorus acid, formic acid, acetic acid, propionic acid, acrylic acid, and methacrylic acid, and the like. As the alkali catalysts, there can be exemplified sodium hydroxide, triethylamine, and ammonia, and the like. Addition amount of the catalysts is preferably 0.0001–5% by weight, particularly, 0.01–0.1% by weight based on total amount of the above-described compounds (H) and (J).

Structure of a polysiloxane portion in the polysiloxane-based macromonomer may be a linearlike, a ladderlike, and a mixed system. In the present invention, of those, there are preferred the ladderlike and mixed system of the linearlike and ladderlike systems and, particularly, there is preferred one having a large amount of the ladderlike portion in view of water resistance, heat resistance, and weatherability, and the like. The structure of the polysiloxane-based macromonomer can be freely selected by a mixing proportion of the compounds (H) and (J), mixing amount of water and the acid catalyst, and the like. In the polysiloxane-based macromonomer to be employed in the present invention, a number average molecular weight is 400–50,000 and, particularly, preferably 1,000–20,000. In the case of less than 400, gelation tends to be caused in copolymerization and, in the case of exceeding 50,000, miscibility tends to lower.

Also, the polysiloxane-based macromonomer in a liquid by the reaction of the compound (H) with the compound (J) contains a polymerizable unsaturated bond of preferably 0.2–1.9 piece, more preferably 0.6–1.4 piece and, particularly 0.9–1.2 piece in the molecule. In the case that the polymerizable unsaturated bond is excessively less, whitening is apt to be caused in a copolymerized reaction product between the polysiloxane-based macromonomer and a vinyl monomer having oxirane group. On the other hand, in the case that the polymerizable unsaturated bond is excessively more, gelation is unpreferably apt to be caused in copolymerization reaction. The number of unsaturated bond in the polysiloxane-based macromonomer is obtained by the following methods.

(1) A variety of polysiloxane-based macromonomers are obtained by appropriately changing the proportion of the compounds (H) and (J), and by allowing to react in identical conditions.

(2) A variety of vinylcopolymers are prepared by allowing to react the respective monomers obtained with a nonfunctional vinyl monomer by changing the proportion to be employed.

(3) Molecular weight distribution in the vinylcopolymers obtained is measured by a gel permeation chromatography (G.P.C.).

(4) Even in the case that there is changed the proportion of the polysiloxane-based macromonomer to the nonfunctional monomer to be employed, a peak molecular weight (a molecular weight of a most large content) in the copolymer obtained is nearly identical, and a distribution curve is a monopeak and, in the case that there are not observed a distribution of components having a low molecular weight (a monomer not having an unsaturated bond component) and a distribution of components having a high molecular weight (a copolymer of a monomer having at least two unsaturated bonds), the monomer has one piece of polymerizable unsaturated bond in the molecule on an average.

(5) In other macromonomer, when use amount by mol number of the compound (H) is [H], and use amount by mol number of the compound (J) is [J], in the case of employing the macromonomer having 1 piece of a polymerizable unsaturated bond on an average, when the mol number of the compound (H) is [H1], and the mol number of the compound (J) is [J1], the average number of the macromonomer having a polymerizable unsaturated bond in the macromonomer is measured by [J]/[H] and [J1]/[H1].

(6) For example, if there is obtained a macromonomer having the number of the polymerizable unsaturated bond of 1 piece in the case of the compound (J)/the compound (H)=1/20 (molar ratio), in the case of the compound (J)/the compound (H)=0.9/20, the number of the polymerizable unsaturated bond becomes 0.9 piece on an average in the macromonomer.

VINYL MONOMER CONTAINING OXIRANE GROUP

The vinyl monomer containing oxirane group which constitutes the component (a) is a compound represented by the formula (6) and, it is prepared by the same preparation process, and has the same structural formula as a compound having $R^2$ represented by the formula (2) or (3) in the compound represented by the formula (1) which is the first aspect of the invention.

Also, as the vinyl monomer containing oxirane group in the present invention, there can be employed together a monomer containing glycidyl group such as glycidylmethacrylate, glycidylacrylate, and vinylglycidyl ether, and the "any one of other alicyclic epoxy compounds containing an unsaturated group" in the second aspect of the invention. Of those, the monomer containing glycidyl group is preferred in view of capability of readily obtaining and costs, and the monomer containing alicyclic oxirane group is preferably employed in view of curability of the low temperature-curable resin composition. These can be employed in a range of 0–80% by mol of the vinyl monomer containing oxirane group to be employed.

The component (a) to be employed for the low temperature-curable resin composition of the present invention is a vinyl copolymer in which there are employed the polysiloxane-based macromonomer and the vinyl monomer containing oxirane group as monomer components. In the copolymer, other polymerizable vinyl monomers can be optionally employed other than the above-described monomer components as monomer components. As the other polymerizable vinyl monomers to be employed, the following compounds are exemplified.

(a) Esters of acrylic acid or methacrylic acid: for example, alkyl esters having a carbon number of 1–18 of acrylic acid or methacrylic acid such as methyl acrylate, ethyl acrylate, propyl acrylate, isopropyl acrylate, butyl acrylate, hexyl acrylate, octyl acrylate, lauryl acrylate, methyl methacrylate, ethyl methacrylate, propyl methacrylate, isopropyl methacrylate, butyl methacrylate, hexyl methacrylate, octyl methacrylate, and lauryl methacrylate; alkoxyalkyl esters having a carbon number of 2–18 of acrylic acid or methacrylic acid such as methoxybutyl acrylate, methoxybutyl methacrylate, methoxyethyl acrylate, methoxyethyl methacrylate, ethoxybutyl acrylate, and ethoxybutyl methacrylate; alkenyl esters having a carbon number of 2–18 of acrylic acid or methacrylic acid such as allyl acrylate and allyl methacrylate; hydroxyalkyl esters having a carbon number of 2–18 of acrylic acid or methacrylic acid such as hydroxyethyl acrylate, hydroxyethyl methacrylate, hydroxypropyl acrylate, and hydroxypropyl methacrylate; alkenyloxyalkyl esters having a carbon number of 3–18 of acrylic acid or methacrylic acid such as allyloxyethyl acrylate and allyloxyethyl methacrylate.

(b) Vinyl aromatic compound: for example, styrene, α-methylstyrene, vinyltoluene, and p-chlorostyrene.

(c) Diene-based compound: for example, butadiene, isoprene, and chloroprene.

(d) Others: acrylonitrile, methacrylonitrile, methyl isopropenyl ketone, Beova monomer of vinyl acetate (a product of Shell Kagaku, Ltd.), vinyl propionate, and vinyl pivarate, and the like.

As copolymerization proportion of the polysiloxane-based macromonomer with respect to the vinyl monomer containing oxirane group, the polysiloxane-based macromonomer is 0.01–98% by weight, the vinyl monomer containing oxirane group is 99.99–2% by weight, more preferably, the polysiloxane-based macromonomer is 0.1–80% by weight, and the vinyl monomer containing oxirane group is 99.9–20% by weight. In the case that the polysiloxane-based macromonomer is less than 0.01% by weight, curability lowers, and, in the case of exceeding 98% by weight, physical properties lower in a cured article, and there is shown a tendency being apt to cause a shrinkage. Also, in the case that the other polymerizable vinyl monomers are employed in addition to the above-described two kinds of monomers as monomer components, the polysiloxane-based macromonomer is 0.01–80% by weight, the vinyl monomer containing oxirane group is 90–1% by weight, other polymerizable vinyl monomers are more than 0 and not more than 98.99% by weight, and more preferably the polysiloxane-based macromonomer is 0.1–60% by weight, the vinyl monomer containing oxirane group is 60–3% by weight, and the other polymerizable vinyl monomers are 10–96.9% by weight. In the case that the use amount of the polysiloxane-based macromonomer and the vinyl monomer containing oxirane group ranges in the scope, no shrinkage is preferably caused.

The above-described vinyl copolymer can be obtained by the same methods and the same conditions as in a synthesis reaction for usual acrylic resins and vinyl resins, and the like. For example, there can be exemplified a method in which respective monomer components are dissolved or dispersed into an organic solvent, and then heated at temperature of 60–180° C. or so under the presence of a radical polymerization initiator while agitating. Reaction time of period is preferably 1–10 hours.

Further, as the organic solvent, there can be exemplified the same alcohol-based solvents, ether-based solvents, ester-based solvents, and hydrocarbon-based solvents, and the like as described in the reaction between the above-described (H) and (J). In the case that the hydrocarbon-based solvents are employed, those are preferably employed together with other solvents in view of solubility.

In a reaction system, a radical initiator can be employed and, as an example, there are shown peroxides such as benzoyl peroxide and t-butylperoxy-2-ethylhexanoate, and azo-compounds such as azoisobutylnitrile and azobisdimethyl valeronitrile.

COMPONENT (B)

The component (b) to be employed in the present invention is a 6-coordinated organic aluminum chelate compound and/or an 8-coordinated organic zirconium chelate compound, and there can be exemplified the following compounds.

As the 6-coordinated organic aluminum chelate compound, there is preferred a compound obtained by treating an organic aluminum with a chelating agent. As the organic aluminum, there is preferred a compound shown by the formula (9) described below.

$$R^{20}\text{—}AlR^{21}R^{22} \qquad (9)$$

(in the formula, at least one of $R^{20}$, $R^{21}$, and $R^{22}$ represent an alkoxyl group having a carbon number of 1–13 or an alkoxyalkoxyl group having a carbon number of 3–10, and other groups represent any of an alkyl group having a carbon number of 1–6, an aryl group, an alkenyl group, and an alkyl group having a carbon number of 1–6 substituted by mercapto group or amino group)

In the formula (9), as the alkoxyl group having a carbon number of 1–13 in $R^{20}$, $R^{21}$, and $R^{22}$, there can be exemplified methoxy, ethoxy, n-propoxy, isopropoxy, n-butoxy, isobutoxy, sec-butoxy, tert-butoxy, n-pentoxy, isoamyloxy, n-hexyloxy, n-heptyloxy, and n-octyloxy. As the alkoxyalkoxyl group having a carbon number of 3–10, there can be exemplified methoxymethoxy, methoxyethoxy, ethoxybutoxy, and butoxypentoxy, and the like.

Further, as the alkyl group having a carbon number of 1–6, there can be exemplified methyl, ethyl, n-propyl, isopropyl, n-butyl, isobutyl, sec-butyl, tert-butyl, and amyl group, as the aryl group, there can be exemplified phenyl or toluyl group, and, as the alkenyl group, there can be exemplified vinyl or allyl group. Still further, as an alkyl group having a carbon number of 1–6 substituted by mercapto group or amino group, there can be exemplified γ-mercaptopropyl group, aminoethyl group, aminopropyl group, and aminobutyl group.

As the preferred 6-coordinated organic aluminum chelate compound, there can be exemplified aluminum isopropylate, aluminum sec-butylate, and aluminum tert-butylate, and the like.

On the other hand, as the chelating agent to be allowed to react with the above-described organic aluminum, there can be exemplified lower alkanol amines, for example, triethanolamine, diethanolamine, and dimethylaminoethanol, and the like, an acetoacetate, for example, acetomethylacetate and acetoethylacetate, and the like, a diketone alcohol, for example, diacetone alcohol, and the like, diketones, for example, acetylacetone, and the like, glycols, for example, ethylene glycol and octylene glycol, and the like, an oxycarboxylic acid, for example, lactic acid and tartaric acid, and the like, a dicarboxylic acid or an ester thereof, for example, maleic acid, ethyl malonate, and the like, and salicylic acid, cathecol, and pyrogallol, and the like. Of those, there are preferred the lower alkanol amines, the oxycarboxylic acid, and the diketones.

As the preferred 6-coordinated organic aluminum chelate compound to be employed in the present invention, there are preferred compounds not having hydroxyl group and an alkoxyl group which directly connect to aluminum atom. In the case that the organic aluminum chelate compound has hydroxyl group and an alkoxyl group which directly connect to aluminum atom, by mixing it with the low temperature-curable resin composition of the present invention, storage stability of a composition becomes unpreferably poor, and smoothness in a coating layer is unpreferably occasionally lowered after curing.

As the preferred 6-coordinated organic aluminum chelate compound to be employed in the present invention, there can be exemplified aluminum tris(ethylacetoacetate), tristrifluoro acetylacetonate aluminum, trishexafluoro acetylacetonate aluminum, trisethylacetoacetate aluminum, tris(n-propyl acetoacetate)aluminum, tris(iso-propyl acetoacetate) aluminum, tris(n-butylacetoacetate)aluminum, trissalycilic aldehydate aluminum, tris(2-ethoxycarbonylphenolate) aluminum, tris(acetyl acetonate)aluminum, tris (ethylacetonate)aluminum, and tris(salicylicaldehydate) aluminum, and the like, and these may be partially condensed.

As the preferred 8-coordinated organic zirconium chelate compound to be employed in the present invention, there are preferred compounds obtained by treating an organic zirconium with a chelating agent, and as the organic zirconium, there is preferred a compound represented by the formula (10) described below,

$$R^{23}—ZrR^{24}R^{25}R^{26} \qquad (10)$$

(in the formula, at least any two of $R^{23}$, $R^{24}$, $R^{25}$, and $R^{26}$ represent an alkoxyl group having a carbon number of 1–13 or an alkoxyalkoxyl group having a carbon number of 3–10, and other groups represent any one of an alkyl group having a carbon number of 1–6, an aryl group, an alkenyl group, and an alkyl group having a carbon number of 1–6 substituted by mercapto group or amino group).

In the formula (10), as the alkoxyl group having a carbon number of 1–13, there can be exemplified methoxy, ethoxy, n-propoxy, isopropoxy, n-butoxy, isobutoxy, sec-butoxy, tert-butoxy, n-pentoxy, isoamyloxy, n-hexyloxy, n-heptyloxy, and n-octyloxy. As the alkoxyalkoxyl group having a carbon number of 3–10, there can be exemplified methoxymethoxy, methoxyethoxy, ethoxybutoxy, and butoxypentoxy, and the like. Further, as the alkyl group having a carbon number of 1–6, there can be exemplified methyl, ethyl, n-propyl, isopropyl, n-butyl, isobutyl, sec-butyl, tert-butyl, and amyl group, as the aryl group, there can be exemplified phenyl or toluyl group, and, as the alkenyl group, there can be exemplified vinyl or allyl group.

Still further, as the alkyl group having a carbon number of 1–6 substituted by mercapto group or amino group, there can be exemplified γ-mercaptopropyl group, aminoethyl group, aminopropyl group, and aminobutyl group.

As the preferred organic zirconium, there can be exemplified tetramethyl zirconate, tetraethyl zirconate, tetraisopropyl zirconate, tetra-n-butyl zirconate, tetraisobutyl zirconate, and tetra-tert-butyl zirconate, and the like.

As the chelating agent to be allowed to react with the above-described organic zirconium compound, there can be preferably employed the same compounds as the chelating compound to be employed in the case of the 6-coordinated organic aluminum compound described hereinabove.

As the organic zirconium chelate compound to be employed in the present invention, there is preferred a compound not having hydroxyl group and an alkoxyl group which directly connect to zirconium atom. In the case of having the hydroxyl group and an alkoxyl group which directly connect to zirconium atom, as well as in the case of the aluminum compounds, there are unpreferably caused a decline of storage stability in a resin composition and a decline of smoothness in a cured coating layer.

As the 8-coordinated organic zirconium chelate compound, there can be exemplified tetraxis(oxalic acid) zirconium, tetraxis(acetylacetone)zirconium, tetraxis(n-propylacetoacetate)zirconium, tetraxis(ethylacetoacetate) zirconium, and tetraxis(salicylic aldehydate) zirconium, and the like, and these may be partially condensed.

COMPONENT (C)

The component (c) to be employed in the present invention is a compound having at least two alicyclic oxirane groups in the molecule and having a number average molecular weight of not more than 1,000, and there can be exemplified compounds described below.

(i) There are compounds shown below including the compound (K).

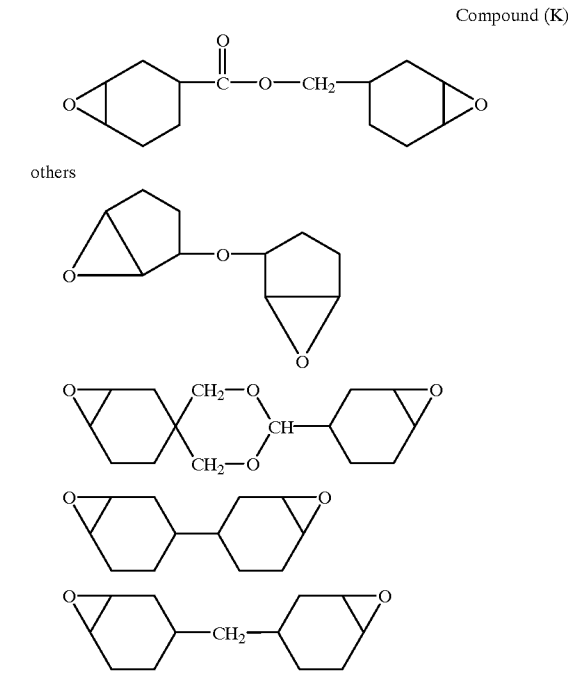

(ii) There is an adduct of 3,4-epoxycyclohexylmethyl alcohol, and the like with a polyisocyanate compound.

As the polyisocyanate compound to be employed, there can be exemplified, for example, an organic diisocyanate itself which includes aliphatic diisocyanates such as hexamethylene diisocyanate or trimethylhexamethylene diisocyanate, alicyclic diisocyanates such as xylilene diisocyanate or isophorone diisocyanate, aromatic diisocyanates such as tolylene diisocyanate or 4,4'-diphenylmethane diisocyanate, or an adduct of the respective diisocyanates with a polyvalent alcohol, a polyester resin having a low molecular weight, or water, a polymer of the above-described respective diisocyanates themselves and, further, an isocyanate-buret compound, and the like. As commercially supplied products, there are "Vernok DN-950", "Vernok D-970", or "Vernok D15-455" which are products manufactured by Dainippon Ink Kagaku, Ltd., "Desmodule L", "Desmodule NHL", "Desmodule IL", or "Desmodule N3390" which are products manufactured by Bayer, AG. in Germany, "Takenate D-102", "Takenate D-202", or "Takenate D-123N" which are products manufactured by Takeda Yakuhin Kogyo, Ltd., "Coronate L", "Coronate HL", "Coronate EH" or "Coronate 203" which are products manufactured by Nihon Polyurethane Kogyo, Ltd., and "Duranate 24A-90CX" which is a product manufactured by Asahi Kasei Kogyo, Ltd.

(iii) There are adducts of the above-described compound (K) with a polybasic acid.

(iv) There are an esterified product having an unsaturated bond in the molecule, for example, such as 4-cyclohexene-1,2-ilene, and a compound which is obtained by oxidation of an esterified compound having a number average molecular weight of 900 which is obtained by an esterification reaction of, for example, tetrahydrophthalic anhydride, trimethylolpropane, and 1,4-butanediol, and the like with peracetic acid, and the like.

Further, as the above-described compound having alicyclic oxirane group, there can be also employed a compound into which there is introduced non-alicyclic oxirane group other than the alicyclic oxirane group.

As a molecular weight of the component (c), it is important that it is not more than 1,000 in a number average molecular weight. In the case that the number average molecular weight exceeds 1,000, there lowers miscibility with the vinyl copolymer resin which is the component (c) to be mixed into the low temperature-curable resin composition of the present invention, resulting in that there cannot be formed a coating layer which is excellent in a finishing property and coatability.

LOW TEMPERATURE-CURABLE RESIN COMPOSITION

The low temperature-curable resin composition of the present invention is composed of the components (a), (b), and (c).

Mixing amount of the component (b) is preferably 0.01–30 parts by weight based on 100 parts by weight of the component (a), in particular, it is preferably 0.1–15 parts by weight. In the case that use amount of the component (b) is less than the range, there is shown a tendency of decline in crosslinking curability and, in the case that it is more than the range, it remains in a cured article, and water resistance unpreferably lowers in the cured article.

Mixing amount of the component (c) is preferably 0.1–1,000 parts by weight based on 100 parts by weight of the component (a), and it is more preferably 5–100 parts by weight. In the case of less than 0.1 part by weight, the content of alicyclic oxirane groups lowers which is an important factor for accelerating curability. Further, the component (c) has a role as a diluent in the low temperature-curable resin composition, and it also contributes to an increase or decrease of the solid content in the low temperature-curable resin composition, and it is desirably mixed in not less than 0.1 part by weight from the viewpoint. It is to be noted that in the case that the mixing amount of the component (c) becomes more than 1,000 parts by weight, curability lowers because of decline in the content of SiOR or/and SiOH groups in the low temperature-curable resin composition.

OTHER COMPONENTS

In the resin composition of the present invention, there can be further optionally mixed, for example, a resin containing epoxy groups ("Epikote 1001" manufactured by Shell Kagaku) and a resin containing hydroxyl groups such as a styrene-allylalcohol copolymer. The resins can be mixed in a mixing amount of not more than 10% by weight based on the low temperature-curable resin composition of the present invention.

USES

A cured article obtained from the low temperature-curable resin composition of the present invention is excellent in weatherability and water resistance, and the like, and it is preferably employed in uses such as, for example, coating or repairing for cars and containers, coating for structural materials in the open air, and a precoat metal, and the like. It is to be noted that in the case of employing as a coating, coating methods are not limited, and it can be coated by a spray coating, a roll coating, and a brush coating, and the like which are usual coating methods.

The low temperature-curable resin composition of the present invention can be employed by dissolving in organic solvents. As the solvents to be employed, there are exemplified a hydrocarbon-based solvent such as toluene and xylene, a ketone-based solvent such as methylethylketone and methylisobutylketone, an ester-based solvent such as ethyl acetate and butyl acetate, an ether-based solvent such as dioxane and ethyleneglycol diethylether, an alcohol-based solvent such as butanol and propanol, and the like. The solvents can be employed solely or by appropriately mixing, and in the case of employing the alcohol-based solvent, it is preferably employed together with other solvents from a viewpoint of solubility to resins. It is to be noted that the concentration of the low temperature-curable resin composition can be appropriately selected according to the purposes of uses and, usually, it is preferably 10–70% by weight.

The low temperature-curable resin composition of the present invention can be readily crosslinked and cured at low temperatures of not more than 100° C. For example, in the case that it is cured at ordinary temperatures without any heating, it can be usually and sufficiently cured for 8 hours to 7 days or so. Further, in the case that it is heated at 40–100° C. or so, it can be sufficiently cured for 5 minutes to 3 hours or so.

Still further, even in the vicinity of ordinary temperatures, it can be sufficiently cured within several tens hours.

It is thought that the curing reaction in the low temperature-curable resin composition of the present invention initiates by volatilization of solvents, and it proceeds as a chain reaction by volatilization of the chelating agent from a crosslinking and curing agent. It is guessed that proceeding of the curing reaction by the crosslinking and curing agent depends upon a mechanism as shown hereinafter. That is, in the case that the organic aluminum chelating agents are employed as the crosslinking and curing agent, first of all, as a first stage reaction after volatilization of the chelating agents, an aluminum compound reacts with the silanol group in the polysiloxane-based macromonomer structural unit to produce the bond of the formula (11) Subsequently, as a second stage reaction, the silanol group coordinates with the bond of the formula (11), and it changes to the formula (12), whereby, the silanol group is polarized. The silanol group polarized reacts with epoxy groups, and it changes to an oxonium salt as in the formula (13). Subsequently, there are caused an ionic polymerization of epoxy groups and addition reaction to hydroxyl group.

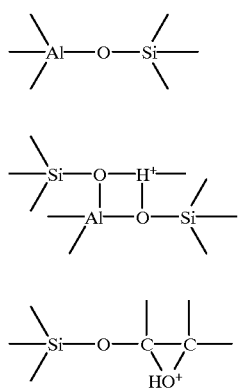

(11)

(12)

(13)

It is guessed that the curing reaction in the low temperature-curable resin composition of the present invention proceeds by simultaneous occurrence of a variety of reactions such as a condensation reaction of silanol groups themselves in addition to the crosslinking reaction by a catalytic action of the above-described crosslinking and curing agent. For example, it is thought that there are caused a variety of curing reactions described below.

(A) Condensation of silanol groups themselves (B) Condensation of a silanol group with hydroxyl group produced from oxirane group (C) Addition of a silanol group to oxirane group (D) Addition of hydroxyl group to oxirane group (E) Ionic polymerization of oxirane groups themselves It is to be noted that in the case that the polysiloxane-based macromonomer structural unit contains an alkoxyl group as a functional group in the low temperature-curable resin composition of the present invention, for example, in the case that it contains an alkoxysilane group, although hydrolysis is required because of producing a silanol group, the hydrolysis reaction sufficiently proceeds by only the presence of a slight amount of water such as moisture in air.

In the low temperature-curable resin composition of the present invention, in the vinyl copolymer to be employed, there exist a functional group such as a silanol in the polysiloxane-based macromonomer and oxirane group in a vinyl monomer containing oxirane group, which are a monomer component.

Therefore, there are simultaneously caused a variety of curing reactions as shown in the above-described (A) to (E).

As results, curing simultaneously proceeds in the surface and inside of a cured article, and it is not apt to cause shrinkage because of a small extent of curing in the surface and inside of a cured article.

EXAMPLES OF FOURTH ASPECT OF THE INVENTION

Hereinafter, although the present invention is specifically illustrated by Examples, the present invention is not limited by those. It is to be noted that "%" represents "% by weight" except a case particularly shown.

Example 1

A SUS-made reaction vessel was charged with 2,720 g (20 mol) of methyltrimethoxysilane, 256 g (1 mol) of γ-methacryloxypropyl trimethoxysilane, 1134 g of deionized water, 2 g of 60%-hydrochloric acid, and 1 g of hydroquinone, and mixture was allowed to react at 80° C. for 5 hours. Polysiloxane-based macromonomer obtained showed a number average molecular weight of 2,000, and it contained one piece of vinyl group (a polymerizable unsaturated bond) and 4 pieces of hydroxyl groups per 1 molecule on an average. There was added dropwise a mixture composed of 300 g of the macromonomer, 100 g of styrene, 280 g of a compound (D) described hereinafter, 400 g of n-butylmethacrylate, 20 g of 2,2'-azobisisobutyronitrile into 1,000 g of xylene at 120° C. to polymerize and obtain a transparent copolymer. A number average molecular weight was approximately 20,000. There were added 30 g of the above-described compound (K) and aluminum tris (ethylacetoacetate) into 140 g of a solution of the copolymer to coat on a glass plate so that dried layer thickness is adjusted to 60μ, followed by baking at 90° C. for 30 minutes. Cured layer was smooth and transparent, shrinkage was not observed, and a residual amount was 92% after extracted by acetone.

Example 2

A SUS-made reaction vessel was charged with 7,800 g (50 mol) of phenyltrisilanol, 200 g (1 mol) of γ-acryloxypropyl trisilanol, and 4,500 g of toluene, and mixture was allowed to react at 117° C. for 3 hours. Polysiloxane-based macromonomer obtained showed a number average molecular weight of 7,000, and it contained one piece of vinyl group and 5–10 pieces of hydroxyl groups per 1 molecule on an average. There was added dropwise a mixture composed of 100 g of the macromonomer, 100 g of 2-hydroxyethylacrylate, 200 g of a compound (L) described hereinafter, 600 g of 2-ethylhexylmethacrylate, 10 g of azoisobutyronitrile into 1,000 g of a mixture composed of equal weight of butanol and xylene at 120° C. to polymerize and obtain a transparent copolymer. A number average molecular weight was approximately 40,000.

There were added 35 g of the above-described compound (K) and 0.3 g of tetraxis(acetylacetone)zirconium into 160 g of a solution of the copolymer to coat on a glass plate so that dried layer thickness is adjusted to 60μ, followed by baking at 80° C. for 30 minutes. Cured layer was smooth and transparent, shrinkage was not observed, and a residual amount was 98.4% after extracted by acetone.

Example 3

There were likewise allowed to react 48 mol of phenyltrimethoxysilane and 2 mol of γ-methacryloxypropyl trimethoxysilane as in the Example 1. Polysiloxane-based macromonomer obtained showed a number average molecular weight of approximately 5,000, and it contained one piece of vinyl group and 5–10 pieces of methoxy groups per 1 molecule on an average.

500 g of the macromonomer and 500 g of the vinyl monomers employed in the Example 1 were likewise allowed to polymerize as in the Example 1 to obtain a copolymer. A number average molecular weight was approximately 60,000. Into 100 g of a solution of the copolymer, there were added 50 g of an adduct of 1 mol of adipic acid with 2 mol of the above-described compound (K) and 1.0 g of aluminum tris(acetylacetone), and it was coated on a glass plate so that dried layer thickness is adjusted to 60μ, followed by baking at 100° C. for 30 minutes. Cured layer was smooth and transparent, shrinkage was not observed, and a residual amount was 96% after extracted by acetone.

Example 4

There were likewise allowed to react 29.1 mol of methyl trimethoxysilane and 0.9 mol of γ-acryloxypropyl triethoxysilane as in the Example 1. Polysiloxane-based macromonomer obtained showed a number average molecular weight of approximately 15,000, and it contained one piece of vinyl group and 5–10 pieces of methoxy groups per 1 molecule on an average. 400 g of the macromonomer and 600 g of vinyl monomers employed in the Example 1 were likewise allowed to react as in the Example 1 to obtain a copolymer. A number average molecular weight was approximately 70,000. 10 g of tetraxis (ethylacetoacetate) zirconium was added into a mixture of 180 g of a solution of the copolymer with 10 g of the above-described compound (K) to coat on a glass plate so that dried layer thickness is adjusted to 60μ, followed by baking at 80° C. for 30 minutes. Cured layer was transparent, shrinkage was not observed, and a residual amount was 94% after extracted by acetone.

Example 5

The curable composition in the Example 2 was coated on a glass plate so that dried layer thickness is adjusted to 60μ, followed by leaving as it is at 25° C. for 48 hours. Cured layer was transparent, shrinkage was not observed, and a residual amount was 95% after extracted by acetone.

Example 6

A SUS-made reaction vessel was charged with 300 g of the macromonomer in the Example 1, 100 g of styrene, 140 g of a compound (L) described hereinafter, 100 g of glycidyl methacrylate, 400 g of n-butylmethacrylate, 20 g of 2,2'-azobisisobutyronitrile. Mixture was added dropwise into 1,000 g of xylene at 120° C. to polymerize and obtain a transparent copolymer. A number average molecular weight was approximately 20,000. There were added 30 g of the above-described compound (K) and aluminum tris (ethylacetoacetate) into 140 g of a solution of the copolymer to coat on a glass plate so that dried layer thickness is adjusted to 60μ, followed by baking at 90° C. for 30 minutes. Cured layer was smooth and transparent, shrinkage was not observed, and a residual amount was 90% after extracted by acetone.

Example 7

A SUS-made reaction vessel was charged with 300 g of the macromonomer obtained in the Example 1, 100 g of styrene, 140 g of a compound (L) described hereinafter, 140 g of a compound (M) described hereinafter, 400 g of n-butylmethacrylate, 20 g of 2,2'-azobisisobutyronitrile. Mixture was added dropwise into 1,000 g of xylene at 120° C. to polymerize and obtain a transparent copolymer. A number average molecular weight was approximately 20,000. There were added 30 g of the above-described compound (K) and aluminum tris(ethylacetoacetate) into 140 g of a solution of the copolymer to coat on a glass plate so that dried layer thickness is adjusted to 60μ, followed by baking at 90° C. for 30 minutes. Cured layer was smooth and transparent, shrinkage was not observed, and a residual amount was 96% after extracted by acetone. It is to be noted that a gel fraction shown by the residual amount after extracted by acetone is represented by wt % of a residual amount in coating layer after extracted at a reflux temperature in a Soxhlet extractor with acetone for 6 hours after a dried coating layer was stripped from the glass plate.

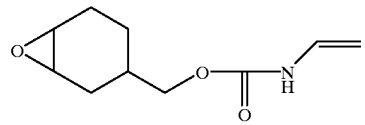

Compound (L)

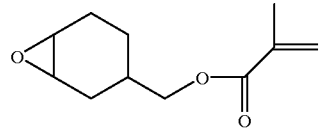

Compound (M)

POSSIBILITIES OF UTILIZATION IN INDUSTRY BY THE FOURTH ASPECT OF THE INVENTION the Invention The low temperature-curable resin composition of the present invention can be readily crosslinked and cured at low temperatures of not more than 100° C., and a cured article having a gel fraction of not less than 95% can be obtained, for example, by only curing at 80° C. for 30 minutes. Further, water is not required in a curing reaction or, a curing reaction proceeds by only the presence of a slight amount of water such as moisture in air. Still further, since a curing initiates by volatilization of solvents, storage stability is excellent even in the case of employing as a one-liquid composition. In curing, a composition having a high solid content can be obtained without using a curing agent having a strong toxicity such as an isocyanate owing to a low solution viscosity in the composition. Also, since there are simultaneously caused a variety of crosslinking reactions such as the condensation reaction of silanol groups and the ionic polymerization reaction of oxirane groups, and the like, the difference of curability in the surface and inside is small, and it is excellent in thick-layer coatability without causing shrinkage. In addition, since by-products in curing are less, there can be obtained a cured article having excellent physical properties, in particular, the cured article is excellent in weatherability and water resistance. There can be obtained a cured article having excellent over-coatability, recoatability, and adhesion, etc. without the presence of uncured portions in the surface of the cured article.

TECHNICAL FIELD OF FIFTH ASPECT OF THE INVENTION

Fifth aspect of the invention relates to a thermosetting type water-based coating composition in which there are mixed a polymer of a specific unsaturated compound containing an epoxy group and a quaternary ammonium compound into a vinyl-based resin, and the like, in particular, it relates to a thermosetting type water-based coating composition which is excellent in storage stability and curability in a coating layer.

BACKGROUND ART OF FIFTH ASPECT OF THE INVENTION

In a water-based coating, water is employed as a medium, and organic solvents are not employed as a medium. Accordingly, there is not anxiety such as a change for the worse in working surroundings and danger of a fire, and it has been widely employed in a variety of fields. For example, as the water-based coating, there has been known a coating in which there is neutralized a resin composition containing a polycarboxylic acid resin having hydroxyl groups and an aminoaldehyde resin with an amine compound, followed by dispersing.

However, conventional water-based coatings require to bake at temperatures of not less than 180° C., and there is a disadvantage that those are poor in chemical and physical properties such as curability, weatherability, and acid resistance. Further, since viscosity of a coating-system increases in storage by gelation, practical water-based coatings cannot be obtained by conventional coatings in which there is employed a bisphenol-epichlorohydrin type epoxy resin instead of the aminoaldehyde resin.

DISCLOSURE OF FIFTH ASPECT OF THE INVENTION

The present inventors, as a result of a repeated intensive investigation for the purpose of obtaining properties well-balanced between storage stability of water-based coatings and curability of a coating layer, have found that the above-described purposes can be attained by a water-based coating composition containing a thermosetting resin composition in which there are mixed a specific epoxy resin and a quaternary ammonium compound into a resin having hydroxyl groups and carboxylic groups, and the present invention was completed.

That is, the present invention provides a thermosetting type water-based coating composition characterized by containing a resin (P) having hydroxyl groups and carboxylic groups, an epoxy resin (Q) prepared by polymerizing an unsaturated compound containing an alicyclic epoxy group represented by the formula (6) described below, and a quaternary ammonium compound (R).

Hereinafter, the present invention will be illustrated in detail.

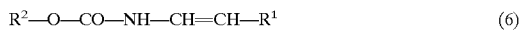

$R^2$—O—CO—NH—CH=CH—$R^1$ (6)

(in the formula, $R^1$ represents a hydrogen atom, an aromatic hydrocarbon group, or a saturated or unsaturated aliphatic hydrocarbon group, and $R^2$ represents formula (2) or formula (3)),

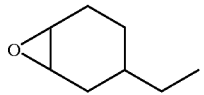 (2)

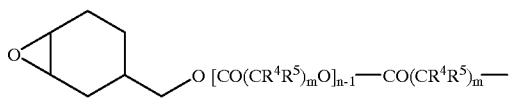 (3)

O [CO(CR$^4$R$^5$)$_m$O]$_{n-1}$—CO(CR$^4$R$^5$)$_m$—

(in the formula, $R^4$ and $R^5$ represent a hydrogen atom, a methyl group or ethyl group, respectively, "m" is an integer of 4–8, and "n" is an integer of 1–10).

BEST MODE FOR CARRYING OUT THE FIFTH ASPECT OF THE INVENTION RESIN (P)

The resin (P) to be employed for the thermosetting type water-based coating composition of the present invention, if it is a resin having hydroxyl groups and carboxylic groups, is not particularly limited. For example, there can be employed every conventional resins which are already known in coating fields such as a vinyl-based resin and a polyester-based resin, and the like, which are employed as a base resin. Specifically, there can be exemplified resins described below.

(1) Vinyl-based resin As the vinyl-based resin, there can be exemplified a copolymer of a vinyl monomer having hydroxyl group with a vinyl monomer having carboxyl group. If a vinyl monomer has hydroxyl group and carboxyl group, there can be also employed a homopolymer thereof.

(i) As the vinyl monomer having hydroxyl group, there can be exemplified monomers having hydroxyl group such as hydroxyethyl(meth)acrylate, hydroxypropyl(meth)acrylate, hydroxybutyl(meth)acrylate, a polycaprolactone diol mono(meth)acrylate, and a polyoxyethyleneglycol mono(meth)acrylate, and the like. These vinyl monomers may be employed solely or in combination of two or more kinds. (ii) As the vinyl monomer having carboxyl group, there can be exemplified (meth)acrylic acid, carboxyethyl (meth)acrylate, itaconic acid, maleic acid, fumaric acid, crotonic acid, and β-carboxyethyl(meth)acrylate, and the like. And others, there can be also employed a modified unsaturated monocarboxylic acid such as an adduct of (meth)acrylic acid with ε-caprolactone. Herein, the modified unsaturated monocarboxylic acid has an unsaturated group and carboxylic group, and if it is a modified unsaturated monocarboxylic acid in which a chain is extended between the unsaturated group and carboxylic group, it is not particularly limited. For example, there can be exemplified a compound shown by formula (A) described hereinafter in which (meth)acrylic acid is modified with a lactone, an unsaturated monocarboxylic acid having ester bonds such as a lactone-modified compound in which terminal hydroxyl groups are modified with an acid anhydride shown by formula (B) described hereinafter, and a compound having carboxyl group such as an modified unsaturated monocarboxylic acid having ether bond shown by formula (C) described hereinafter.

Further, together with the vinyl monomer having carboxyl group, optionally, there can be exemplified a copolymer of a monomer having a radically polymerizable unsaturated group such as methyl(meth)acrylate, ethyl(meth)acrylate, i-propyl(meth)acrylate, n-butyl(meth)acrylate, 2-ethylhexyl (meth)acrylate, acrylonitrile, acrylamide, styrene, vinyltoluene, vinylacetate, i-propylvinylether, n-butylvinylether, and methoxyethylvinylether which do not have a functional group which reacts to hydroxyl group and carboxyl group. It is to be noted that the respective monomers may be employed solely or in combination of two or more kinds.

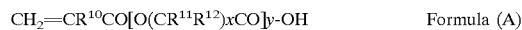
$CH_2=CR^{10}CO[O(CR^{11}R^{12})xCO]y$-OH  Formula (A)

$CH_2=CR^{10}COOCH_2CH_2O[CO(CR^{11}R^{12})xO]$
$yCOR^{13}C$ OOH  Formula (B)

$CH_2=CR^{10}COO[(CR^{14}R^{15})xO]yCOR^{13}COOH$  Formula (C)

(in the formulae, $R^{10}$ represents a hydrogen atom or a methyl group, $R^{11}$ and $R^{12}$ represent a hydrogen atom, a methyl group, or an ethyl group, respectively, and $R^{13}$ represents a divalent aliphatic saturated or unsaturated hydrocarbon group having a carbon number of 1–10, a divalent alicyclic saturated or unsaturated hydrocarbon group having a carbon number of 1–6, p-xylilene group, or phenylene group, and $R^{14}$ and $R^{15}$ represent a hydrogen atom, a methyl group, an ethyl group, a propyl group, and a butyl group, respectively, x is an integer of 4–8, and y is an integer of 1–10)

(2) Polyester-based resin

As the polyester-based resin, there can be exemplified a polyester resin obtained by a polycondensation of polyol components such as trimethylolethane, trimethylolpropane, pentaerythritol, glycerine, ethyleneglycol, propyleneglycol, 1,3-butyleneglycol, neopentylglycol, and 1,6-hexanediol with polycarboxylic acid components such as phthalic acid (anhydride), isophthalic acid, tetrahydrophthalic acid, hexahydrophthalic acid, adipic acid, and trimellitic acid (anhydride); a resin in which the polyester resin is modified with an aliphatic acid or an epoxy resin; an acryl-grafted modified polyester resin; a modified polyester resin obtained by adding acid anhydrides such as maleic anhydride to an esterified product in which a bisphenol-epichlorohydrin type epoxy resin is modified by an aliphatic acid and the like; a resin in which polycarboxylic acids and the like are added to a product in which a bisphenol-epichlorohydrin type epoxy resin is polymerized under the presence of catalysts.

Of the above-described resins (P), there is particularly preferred the vinyl-based resin obtained by polymerizing a vinyl monomer having hydroxyl group with a vinyl monomer having carboxyl group, and optionally, other monomers.

Also, in the resins (P), a number average molecular weight is 1,000–100,000, in particular, preferably 2,000–80,000, and a softening point is not more than 130° C., in particular, preferably not more than 115° C. Acid value is 1–100, in particular, preferably 10–80, and a hydroxyl group value is 10–5,000, in particular, preferably 20–2,000. In the case that the number average molecular weight is smaller than 1,000, there are apt to unpreferably lower properties in a coating layer such as hardness, bending resistance, and corrosion resistance and, on the other hand, in the case that the number average molecular weight is more than 100,000, there tend to become unpreferably worse outer appearances in a coating layer such as smoothness.

Further, in the case that the softening point is higher than 130° C., there is apt to become unpreferably worse smoothness in a coating layer. Still further, in the case that the acid value is smaller than 1, there is apt to become unpreferably difficult a change to a water-based property and, on the other hand, in the case that the acid value is more than 100, there becomes unpreferably worse a storage stability in a coating. In the case that the hydroxyl group value is smaller than 10, there unpreferably lowers curability in a coating, and there is unpreferably observed a tendency of decline of properties in a coating layer such as hardness and bending resistance and, on the other hand, in the case that the hydroxyl group value is more than 5,000, there unpreferably lower properties in a coating layer such as water resistance and corrosion resistance.

In the resins (P), in addition to hydroxyl group and carboxyl group, there can also be optionally introduced functional groups such as a phenolic hydroxyl group, an alkoxysilane group, and a hydroxysilane group. There is not particularly limited a method in order to introduce the functional groups, and already known methods can be employed. For example, introduction of the phenolic hydroxyl group may be conducted by copolymerizing using a bisphenol-modified (meth)acrylate as the vinyl monomer component in the above-described vinyl-based resin, and introduction of the alkoxysilane group and the hydroxysilane group may be conducted by copolymerizing using a compound such as γ-methacryloxypropyl trimethoxysilane and a hydrolyzed product thereof as the vinyl monomer component in the above-described vinyl-based resin.

EPOXY RESIN (Q)

The epoxy resin (Q) to be employed in the coating composition of the present invention is a polymer of the unsaturated compound containing an alicyclic epoxy group represented by the above-described formula (6), that is, a polymer of a compound which is prepared by the same process and, which has the same structural formula as a compound in which $R^2$ is represented by the formula (2) or (3) in the compound represented by the formula (1) of the first aspect of the invention. It is to be noted that in addition to the above-described unsaturated compound containing an alicyclic epoxy group, there can be also copolymerized "any one of other alicyclic epoxy compounds containing an unsaturated group" in the second aspect of the invention.

In the epoxy resin (Q), in addition to the unsaturated compound containing an alicyclic epoxy group and the above-described other compounds, there can be also copolymerized a radically-polymerizable monomer containing an unsaturated group such as methyl(meth)acrylate, ethyl (meth)acrylate, i-propyl (meth)acrylate, n-butyl(meth) acrylate, 2-ethylhexyl (meth)acrylate, acrylonitrile, acrylamide, styrene, vinyltoluene, vinylacetate, i-propylvinylether, n-butylvinylether, and methoxyethylvinylether, which do not have functional groups which cause a reaction with hydroxyl group and carboxyl group.

In the epoxy resin (Q), a number average molecular weight is 194–100,000, particularly 194–2,000 and, in particular, preferably 194–1,000, epoxy equivalent is 50–2,000 and, in particular, preferably 55–1,000, a softening point is not more than 130° C. and, in particular, preferably 115° C. It is difficult to obtain a compound having a number average molecular weight of smaller than 100 and, on the other hand, in a compound having a number average molecular weight of larger than 100,000, since smoothness becomes worse in surface of a coated layer, it is not preferred so much. It is difficult to obtain a compound having an epoxy equivalent of smaller than 50 and, on the other hand, in a compound having an epoxy equivalent of larger than 2,000, curability tends to lower in a coating layer. Further, in a compound having a softening point of higher than 130° C., smoothness is apt to become worse in a coating layer.

In combination with the above-described epoxy resin (Q), there can be also employed a compound having at least two of at least one or more kinds of epoxy groups selected from an epoxy group at an alicyclic hydrocarbon ring or an epoxy group which directly connects to carbon atom by which an alicyclic hydrocarbon ring is formed, in the molecule. The alicyclic hydrocarbon ring may be a small ring of a three-membered ring to a seven- or more-membered ring and, the ring may be a single-ring or multi-ring, and further, the ring may form an organic hydrocarbon ring. As specific examples of the epoxy resin (Q) to be employed together, there can be exemplified epoxy resins having bifunctionality or more functionalities as shown below.

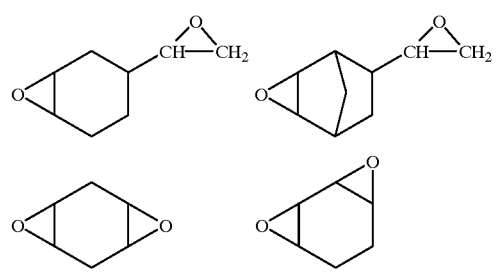

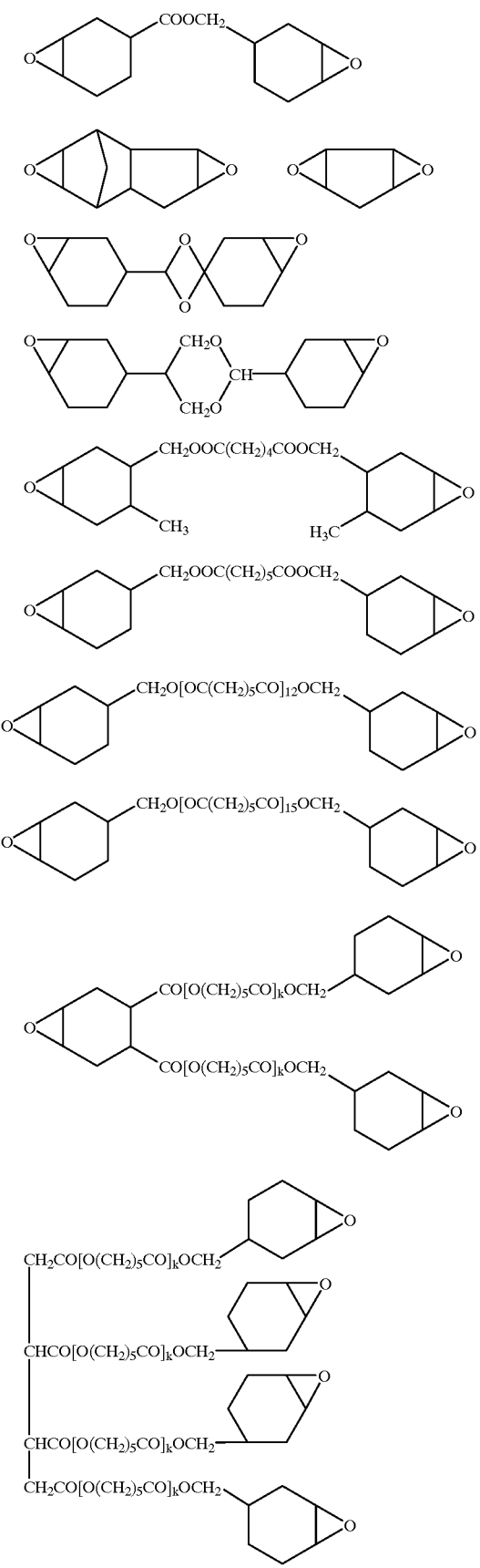

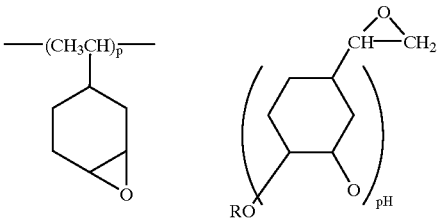

(in the formula, "k" is an integer of 0–15, and "p" is an integer of 2–100)

In combination with the above-described epoxy resin (Q), further, there can be also employed other epoxy resins having an epoxy group such as a glycidyl ether type epoxy resin and an aliphatic inner epoxy resin. The other epoxy resins are preferably employed in a proportion of not more than 25% by weight based on the total amount of both compounds from a viewpoint of storage stability of a coating and curability in a cured coating layer.

QUATERNARY AMMONIUM COMPOUND

As the quaternary ammonium compound (R) to be employed in the coating composition of the present invention, there can be employed a compound shown by $(R^{20}R^{21}R^{22}R^{23}N^{(+)})X^{(-)}$.

In the formula, $R^{20}$, $R^{21}$, $R^{22}$, and $R^{23}$ represent a hydrocarbon group, respectively, and which may be identical or different from each other. Further, the hydrocarbon group may be also substituted by hydroxyl group. X represents a halogen ion or an anionic residual group of an acid, for example, there can be exemplified Cl, Br, F, I, $SO_4$, $HSO_4$, $NO_3$, $PO_4ClO_4$, HCOO, $CH_3COO$, and OH, and the like.

As the preferred quaternary ammonium compound (R) to be employed in the present invention, there can be exemplified the following compounds.

(i) There can be exemplified tetraalkyl ammonium halides such as tetramethyl ammonium chloride, tetraethyl ammonium chloride, tetrabutyl ammonium chloride, methyltriethyl ammonium chloride, tetramethyl ammonium bromide, tetraethyl ammonium fluoride, and tetraethyl iodide (ii) There can be exemplified tetraalkyl ammonium salts of an organic acid such as tetramethyl ammonium acetate and tetraethyl ammonium formate.

(iii) There can be exemplified tetraalkyl ammonium salts of an inorganic acid such as tetramethyl ammonium hydrosulphate, tetraethyl ammonium hydrosulphate, tetramethyl ammonium nitrate, tetraethyl ammonium nitrate, tetraethyl ammonium perchlorate, and tetraethyl ammonium phosphate.

(iv) There can be exemplified quaternary ammonium hydroxides such as tetramethyl ammonium hydroxide, tetraethyl ammonium hydroxide, tetrapropyl ammonium hydroxide, tetrabutyl ammonium hydroxide, tetrapentyl ammonium hydroxide, tetraisoamyl ammonium hydroxide, tetradodecyl ammonium hydroxide, methyltriethyl ammonium hydroxide, ethyltrimethyl ammonium hydroxide, decyltrimethyl ammonium hydroxide, monohydroxyethyl trimethylammonium hydroxide, monohydroxyethyl triethylammonium hydroxide, dihydroxyethyl dimethyl ammonium hydroxide, dihydroxyethyl diethyl ammonium hydroxide, trihydroxyethyl monomethyl ammonium hydroxide, trihydroxyethyl monoethyl ammonium hydroxide, benzyltrimethyl ammonium hydroxide, benzyltriethyl ammonium hydroxide, benzylmethyldiethyl ammonium hydroxide, and cyclohexyltrimethyl ammonium hydroxide.

Of those, the quaternary ammonium hydroxides are particularly preferred in view of readily dispersing the resin (P) and the epoxy resin (Q) into water, and providing a coating composition having an excellent storage stability, and moreover, capability of forming a coating layer which is excellent in water resistance and corrosion resistance.

THERMOSETTING TYPE WATER-BASED COATING COMPOSITION

In the thermosetting type water-based coating composition of the present invention, the resin (P) is mixed in 40–97% by weight, preferably 50–95% by weight, and more preferably, 60–90% by weight, and the epoxy resin (Q) is mixed in 3–60% by weight, preferably 5–50% by weight, and more preferably, 10–40% by weight based on the total amount of the resin (P) and the epoxy resin (Q). In the case that the resin (P) is less than 40% by weight and the epoxy resin (Q) is more than 60% by weight, dispersibility into water lowers in a coating composition obtained. On the other hand, in the case that the resin (P) is more than 97% by weight and the epoxy resin (Q) is less than 3% by weight, there lower properties in a coating layer such as water resistance, corrosion resistance, and bending resistance.

Also, the epoxy resin (Q) is preferably mixed with the resin (P), so that an equivalent ratio (hydroxyl groups/epoxy groups) of hydroxyl groups in the resin (P) becomes not less than 0.3, preferably, 0.5–5, and more preferably 0.7–4 based on epoxy groups in the epoxy resin (Q). In the case that the equivalent ratio is less than 0.3, unreacted components in the resin (P) become large in a coating layer, resulting in that there occasionally lower properties in a coating layer such as bending resistance, water resistance, and corrosion resistance. Further, the epoxy resin (Q) can be stably dispersed into water by carboxyl groups in the resin (P), and mixing proportion thereof is a range of 0.1–1, particularly, preferably 0.1–0.6 as an equivalent ratio of carboxyl groups to epoxy groups from a viewpoint of dispersion into water and storage stability of a coating. The quaternary ammonium compound (R) is preferably employed in a range of 0.01–10% by weight, preferably 0.1–7% by weight, and more preferably, 0.1–5% by weight based on the total amount of the resin (P), the epoxy resin (Q), and the quaternary ammonium compound (R). In the range, there can be obtained a resin having sufficient weatherability and acid resistance.

As a method for the preparation of the thermosetting type water-based coating composition of the present invention, the following methods are exemplified.

First of all, the epoxy resin (Q) or a solution in which the epoxy resin (Q) is dissolved or dispersed in an organic solvent is mixed into a solution in which the resin (P) is dissolved or dispersed in an organic solvent. Subsequently, the quaternary ammonium compound (R) and optionally a neutralizing agent are mixed into a mixture obtained, followed by dispersing into water to prepare. As organic solvents to be employed in order to dissolve or disperse the above-described resin (P) or the epoxy resin (Q), there is preferred an organic solvent which is substantially inert to functional groups in the resins and, specifically, there are exemplified alcohol-based solvents, ether-based solvents, ketone-based solvents, ester-based solvents, and hydrocarbon-based solvents, and the like. Of those, there are preferably employed hydrophilic solvents such as alcohol-based solvents and ether-based solvents as a main solvent. Further, as the neutralizing agent, there can be employed, for example, ammonia, trimethylamine, triethylamine, tributylamine, dimethylethanol amine, diethylethanolamine, dimethylpropanolamine, methyldiethanol amine, ethyldiethanol amine, and triethanol amine, and the like. It is to be noted that in the case that the quaternary ammonium hydroxide is employed as the quaternary ammonium compound (R), resin components can be dispersed into water without the use of the neutralizing agent.

Also, there may be optionally employed the quaternary ammonium compound (R) in combination with the above-described neutralizing agents.

In the coating composition of the present invention, there can be mixed other compounds. As resins to be mixed, there can be also mixed a polyol resin not containing carboxylic groups such as a polytetramethylene glycol, a bisphenol A-ethyleneoxide adduct, a polycaprolactone polyol, a polycarbonatediol, a polyurethane polyol, a vinylalcohol (co)polymer, and a styrene-allylalcohol copolymer. As a catalyst for the purpose of curing a coating layer at lower temperatures, there can be exemplified a phenol compound such as catechol, a silanol compound such as diphenylsilanediol, a metallic chelating compound composed of chelating compounds of metals such as Al, Ti, V, Fe, Zn, Zr, and Sn with β-diketone such as acetoethylacetate, trifluoroacetyl acetone, and dibenzoylacetyl acetone. The catalyst is preferably mixed within a range of 0.01–10 parts by weight based on 100 parts by weight of the total amount of the resin (P) and the epoxy resin (Q). Further, there can be optionally mixed coloring pigments such as a Titanium White, Carbon Black, and red iron oxide, extender pigments such as clay, talc, and silica, dispersants for pigments, an anti-repelling agent, a fluidity modifier, and the like, which are additives for coatings.

There is not particularly limited a method for forming a coating layer using the coating composition of the present invention. For example, it can be conducted by coating on the surface of a base material by a means such as an electro-deposition coating, a spray coating, an immersion coating, a roller coating, and brush coating, followed by drying.

Thickness of coating layer is not particularly limited, and it is usually sufficiently employed within a range of 10–100 μm.

Drying of the coating layer can be preferably conducted in a range of 0–200° C., and more preferably 50–180° C. It can be conducted at 120° C. for 30 minutes or so, and at 180° C. for 10 minutes or so. The base material to be coated is not also particularly limited, and there can be preferably employed a wide range of metals such as a steel, aluminum, Alumite, copper, a metal-plated steel in which the surface is plated by zinc, chromium, and aluminum, and the like, a steel in which the surface of an iron is chemically-treated by chromic acid and phosphoric acid, or electrolytically-treated.

EXAMPLES OF FIFTH ASPECT OF THE INVENTION

Hereinafter, although the present invention is specifically illustrated by Examples, the present invention is not limited by those. It is to be noted that "part" represents "part by weight" except a case particularly shown, and "%" represents "% by weight" except a case particularly shown.
Method for measurements (1) Storage Stability: A state of sedimentation and separation in a dispersed product was visually observed after placing for 1 month at 30° C., and a case was judged as no-abnormal, in which there is not caused a color change by sedimentation of a dispersant in a coating composition.

(2) Smoothness in a coating layer: An uneven state of the surface in a coating layer was visually observed, and a case was judged excellent, in which gloss exists in the surface.

(3) Salt spray resistance: It was tested according to JIS Z-2371, there was judged qualified a sample having a creep width of not exceeding 2 mm in one side from a cut portion in a coating layer. Test time was 1000 hours.

(4) Pencil hardness: It was tested according to JISK-5400.

(5) Bending resistance: A test plate was bent at a right angle within 1–2 seconds at an atmosphere of 20° C., and there was judged qualified the absence of abnormality such as peel or crack of a coating layer in a bent portion.

(6) Gel fraction: A dried coating layer was stripped and put in a net-like vessel having 300 mesh made by a stainless steel, and an extraction was conducted by a soxhlet extractor at a reflux temperature for 6 hours using a mixed solvent of acetone/methanol=1/1, followed by calculating the gel fraction according to the following equation. Gel fraction (%) was evaluated by "the weight of coating layer after being extracted"/"the weight of coating layer before being extracted".

Example 1

A 4-necked flask was charged with 75 parts of methyl propanol, followed by heating to 110° C. Into the flask, there were added dropwise over 1 hour a mixture composed of 3 parts of acrylic acid, 20 parts of hydroxyethylacrylate, 57 parts of methylmethacrylate, and 20 parts of styrene, and a mixture composed of 1 part of 2,2'-azobisisobutylnitrile and 5 parts of methylisobutyl ketone. Aging was conducted for 1.5 hour to obtain a resin solution (P) having an acid value of 23, a hydroxyl value of 97, a number average molecular weight of 20000, and the solid content of 55%. Subsequently, a 4-necked flask was charged with 25 parts of methylpropanol, followed by heating to 110° C., and followed by adding dropwise a mixture composed of 25 parts of the compound (S) described below, a mixture composed of 5 parts of 2,2'-azobisisobutylnitrile and 5 parts of methylisobutyl ketone over 3 hours. Aging was further conducted for 3 hours to obtain a resin solution (Q) having an epoxy equivalent of 200, an average molecular weight of approximately 3,000, and the solid content of 42%. 19.5 parts of 20% solution of tetraethyl ammonium hydroxide was added into 181 parts of the above-described resin solution (P) and 60 parts of the (Q), followed by adding 166 parts of a deionized water while agitating to obtain a water-dispersed product having the solid content of 30% and an average particle size of 0.15 μm. The storage stability in the water-dispersed product obtained was not abnormal in both of a coatings state and properties of a coating layer. Further, the water-dispersed product before the storage stability test was coated in the thickness in a dried layer of 20 μm by spraying on a steel plate treated by zinc phosphate, followed by drying at 80° C. for 10 minutes and further drying at 120° C. for 20 minutes to obtain a coated product. In the coated product, the smoothness of a coating layer was excellent, and the salt spray resistance was also passed, the pencil hardness was H, and the bending resistance was also passed. The gel fraction in the coating layer was 97%.

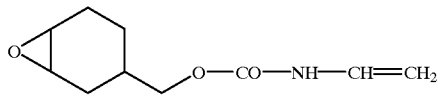

Compound (S)

Example 2

A 4-necked flask was charged with 64 parts of methylpropanol, followed by heating to 110° C. Into the flask, there were added dropwise over 1 hour a mixture composed of 4 parts of methacrylic acid, 25 parts of hydroxyethylmethacrylate, 10 parts of 2-ethylhexyl methacrylate, 51 parts of methylmethacrylate, and 10 parts of styrene, and a mixture composed of 1 part of 2,2'-azobisisobutylnitrile and 5 parts of methylisobutyl ketone. Aging was further conducted for 1.5 hour to obtain a resin solution (P) having an acid value of 26, a hydroxyl value of 108, a number average molecular weight of 25,000, and the solid content of 59%. Subsequently, a 4-necked flask was charged with 25 parts of methylpropanol, followed by heating to 110° C., and followed by adding dropwise a mixture composed of 10 parts of the above-described compound (S) and 5 parts of the compound (T) described below, and a mixture composed of 5 parts of 2,2'-azobisisobutylnitrile and 5 parts of methylisobutyl ketone over 3 hours. Aging was further conducted for 3 hours to obtain a resin solution (Q) having an epoxy equivalent of 200, an average molecular weight of approximately 3,000, and the solid content of 30%. 16.2 parts of 10% solution of tetramethyl ammonium hydroxide was added into 170 parts of the above-described resin solution (P) and 60 parts of the (Q), followed by adding 148 parts of a deionized water while agitating to obtain a water-dispersed product having the solid content of 30% and an average particle size of 0.18μ. The storage stability of the water-dispersed product obtained was not abnormal in both of a coatings state and properties of a coating layer. The water-dispersed product before the storage test was likewise coated and dried to obtain a coated product, and the smoothness of a coating layer in the coated product was excellent, and the salt spray resistance was also passed, the pencil hardness was 3H, and the bending resistance also passed. It is to be noted that the gel fraction in the coating layer was 97%.

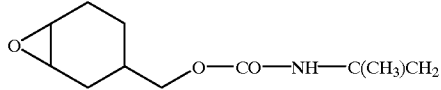

Compound (T)

Example 3

160 parts of a deionized water was added into a mixture composed of 150 parts of 55%-resin solution (P) obtained in the Example 1, 10 parts of 42%-resin solution (Q) obtained in the Example 1, 10 parts of 3,4-epoxycyclohexylcarboxymethyl cyclohexeneoxide, 17.9 parts of 10%-solution of tetrabutyl ammonium hydroxide, and 2 parts of triethylamine while agitating to obtain a water-dispersed product having the solid content of 27% and an average particle size of 0.1 μm. The storage stability in the water-dispersed product obtained was not abnormal in both of a coatings state and properties of a coating layer.

Further, the water-dispersed product before the storage stability test was coated in the thickness of 20 μm in a dried layer by spraying onto a steel plate treated by zinc phosphate, followed by drying at 80° C. for 10 minutes and further drying at 140° C. for 20 minutes to obtain a coated product. In the coated product, the smoothness of a coating layer was excellent, and the salt spray resistance was also passed, the pencil hardness was 2H, and the bending resistance also passed. It is to be noted that the gel fraction in the coating layer was 93%.

Comparative Example 1

The same procedures were followed as in the Example 1 except that 20 parts of hydroxyethylacrylate and 57 parts of methylmethacrylate in the Example 1 were changed to 77 parts of methylmethacrylate, and 19.5 parts of 20% solution of tetrahydroxy ammonium hydroxide was changed to 3.4 parts of triethylamine, respectively, and 166 parts of a deionized water in the Example 1 was changed to 180 parts to obtain a water-dispersed product having the solid content of 30%. The storage stability was not abnormal in the water-dispersed product obtained. Further, the water-dispersed product before storage was likewise coated and dried as in the Example 1 to obtain a coated product. Although the smoothness of a coating layer was excellent in the coated product, the salt spray resistance did not pass, and the pencil hardness was 4B, and the bending resistance did not also pass. It is to be noted that the gel fraction in the coating layer was 55%.

POSSIBILTIES OF UTILIZATION IN INDUSTRY BY THE FIFTH ASPECT OF THE INVENTION

In the thermosetting type water-based coating composition of the present invention, there does not almost proceed a reaction of functional groups themselves which are hydroxyl groups in the resin (P) and epoxy groups in the epoxy resin (Q) at the vicinity of room temperatures, and when it is baked at the vicinity of 100° C., there abruptly proceeds the reaction of functional groups themselves. Therefore, it is particularly excellent in the storage stability and a low-temperature curability of a coating layer. Also, the smoothness is excellent in a cured coating layer formed from the thermosetting type water-based coating composition of the present invention, and it is excellent in the salt spray resistance and the bending resistance.

What is claimed is:
1. A compound represented by formula (1),

$$R^2-O-CO-NH-CH=CH-R^1 \quad (1)$$

wherein $R^1$ represents a hydrogen atom, an aromatic hydrocarbon group, or a saturated or unsaturated aliphatic hydrocarbon group, and wherein $R^2$ represents an aliphatic hydrocarbon group having a reactive functional group for thermosetting or photocuring.

2. A compound as claimed in claim 1, wherein said group containing a reactive functional group is a group containing an alicyclic epoxide.

3. A compound as claimed in claim 1, wherein said aliphatic hydrocarbon group substituted by a group containing a reactive functional group is a group represented by formula (2) or (3),

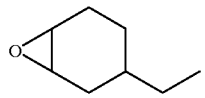

(2)

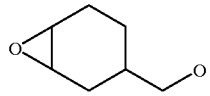

(3)

wherein $R^4$ and $R^5$ represent a hydrogen atom, a methyl group or ethyl group, respectively, "m" is an integer of 4–8, and "n" is an integer of 1–10.

4. A polymer of a compound as claimed in any one of claims 1–3.

5. A process for the preparation of a compound as claimed in claim 1 which comprises allowing to react a compound having a hydroxyl group represented by formula (4-1) or (4-2) with a compound represented by formula (5),

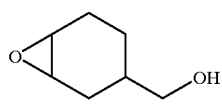

(4-1)

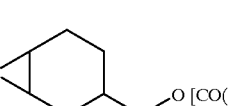

(4-2)

wherein $R^4$ and $R^5$ represent a hydrogen atom, a methyl group or ethyl group, respectively, "m" is an integer of 4–8, and "n" is an integer of 1–10, $$N_3-CO-CH=CH-R^1 \quad (5)$$

wherein $R^1$ represents a hydrogen atom, an aromatic hydrocarbon group, or a saturated or unsaturated aliphatic hydrocarbon group.

6. An active energy ray-curable type unsaturated resin composition which comprises mixing a reaction product of an unsaturated compound containing an alicyclic epoxy group represented by formula (6) with an unsaturated resin containing acid groups, with a diluent, $$R^2-O-CO-NH-CH=CH-R^1 \quad (6)$$

wherein $R^1$ represents a hydrogen atom, an aromatic hydrocarbon group, or a saturated or unsaturated aliphatic hydrocarbon group, $R^2$ represents formula (2) or formula (3),

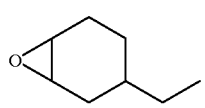

(2)

-continued

(3)

wherein $R^4$ and $R^5$ represent a hydrogen atom, a methyl group or ethyl group, respectively, "m" is an integer of 4–8, and "n" is an integer of 1–10.

7. An active energy ray-curable type unsaturated resin composition as clamed in claim 6, wherein said unsaturated resin containing acid groups is an acrylic-based resin containing acid groups.

8. An alkali developable and active energy ray-curable type resist resin composition which comprises an active energy ray-curable type unsaturated resin composition as claimed in claim 6 or 7.

9. An active energy ray-polymerizable unsaturated resin composition obtainable by allowing to react an unsaturated compound (E) containing an alicyclic epoxy group represented by formula (6) with a colloidal silica (F) in the presence of a metal chelate and/or metal alkoxide (G), $$R^2-O-CO-NH-CH=CH-R^1 \quad (6)$$

wherein $R^1$ represents a hydrogen atom, an aromatic hydrocarbon group, or a saturated or unsaturated aliphatic hydrocarbon group, $R^2$ represents formula (2) or formula (3),

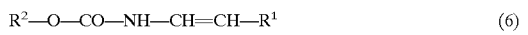

(2)

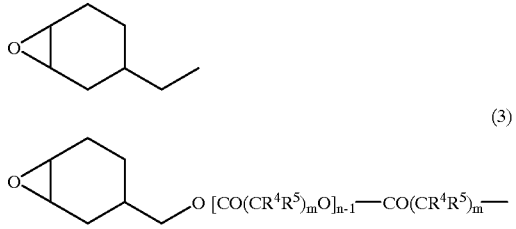

(3)

wherein $R^4$ and $R^5$ represent a hydrogen atom, a methyl group or ethyl group, respectively, "m" is an integer of 4–8, and "n" is an integer of 1–10.

10. A powder-state active energy ray-polymerizable unsaturated resin composition obtained by removing a solvent from an active energy ray-polymerizable unsaturated resin composition as claimed in claim 9.

11. An active energy ray-curable composition which comprises an active energy ray-polymerizable unsaturated resin composition as claimed in claim 9.

12. A powder-state active energy ray-curable composition which comprises a powder-state active energy ray-polymerizable unsaturated resin composition as claimed in claim 10.

13. A low temperature-curable resin composition characterized by containing the following components (a), (b), and (c), (a) a vinyl copolymer having a number average molecular weight of 2,000–100,000 which is a copolymer of a polysiloxane-based macromonomer having a number average molecular weight of 400–50,000 containing at least two hydroxyl groups or alkoxyl groups in the molecule with a vinyl monomer containing oxirane group represented by formula (6), said macromonomer being obtained by allowing to react 70–99.999% by mol of a compound (H) represented by formula (7) with 30–0.001% by mol of a compound (J) represented by formula (8), (b) a 6-coordinated organic aluminum chelate compound and/or an 8-coordinated organic zirconium chelate compound, (c) a compound having a number average molecular weight of not more than 1,000 containing at least two alicyclic oxirane groups in the molecule,

(7)

wherein $R^{11}$ represents an aliphatic hydrocarbon group having a carbon number of 1–8 or a phenyl group, $R^{12}$, $R^{13}$, and $R^{14}$ represent an alkoxyl group having a carbon number of 1–4 or a hydroxyl group, $$CH_2=CR^{15}COO(CH_2)_k-SiR^{16}R^{17}R^{18} \quad (8)$$

wherein $R^{15}$ represents a hydrogen atom or a methyl group, $R^{16}$, $R^{17}$, and $R^{18}$ represent any one of a hydroxyl group, an alkoxyl group having a carbon number of 1–4, and an aliphatic hydrocarbon group having a carbon number of 1–8, "k" is an integer of 1–6, and all the $R^{16}$, $R^{17}$, and $R^{18}$ are not simultaneously an aliphatic hydrocarbon group having a carbon number of 1–8, $$R^2-O-CO-NH-CH=CH-R^1 \quad (6)$$

wherein $R^1$ represents a hydrogen atom, an aromatic hydrocarbon group, or a saturated or unsaturated aliphatic hydrocarbon group, and $R^2$ represents formula (2) or formula (3),

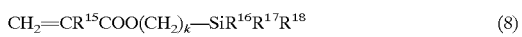

(2)

(3)

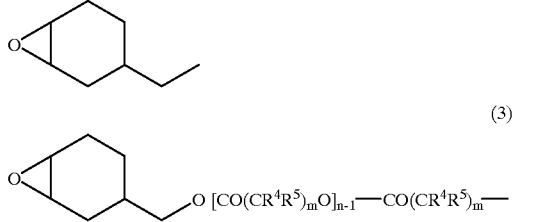

wherein $R^4$ and R represent a hydrogen atom, a methyl group or ethyl group, respectively, "m" is an integer of 4–8, and "n" is an integer of 1–10.

14. A thermosetting type water-based coating composition characterized by containing the following components (P), (Q), and (R), (P) a resin having hydroxyl groups and carboxylic groups, (Q) an epoxy resin prepared by polymerizing an unsaturated compound containing an alicyclic epoxy group represented by the formula (6) as claimed in claim 13, (R) a quaternary ammonium compound.

* * * * *